United States Patent
Dauty et al.

(10) Patent No.: US 9,278,131 B2
(45) Date of Patent: Mar. 8, 2016

(54) PROCESS FOR LOWERING THE VISCOSITY OF HIGHLY CONCENTRATED PROTEIN SOLUTIONS

(71) Applicant: ADOCIA, Lyons (FR)

(72) Inventors: Emmanuel Dauty, Lyons (FR); Thomas Ballet, Lyons (FR); Remi Soula, Lyons (FR)

(73) Assignee: ADOCIA, Lyons (FR)

( * ) Notice: Subject to any disclaimer, the term of this patent is extended or adjusted under 35 U.S.C. 154(b) by 323 days.

(21) Appl. No.: 13/962,324

(22) Filed: Aug. 8, 2013

(65) Prior Publication Data

US 2014/0044708 A1 Feb. 13, 2014

Related U.S. Application Data

(60) Provisional application No. 61/682,003, filed on Aug. 10, 2012.

(30) Foreign Application Priority Data

Aug. 10, 2012 (FR) ...................................... 12 57775

(51) Int. Cl.
| | | |
|---|---|---|
| A61K 47/18 | (2006.01) | |
| A61K 47/16 | (2006.01) | |
| A61K 39/395 | (2006.01) | |
| C07K 16/22 | (2006.01) | |
| C07K 16/24 | (2006.01) | |
| C07K 16/28 | (2006.01) | |
| A61K 9/00 | (2006.01) | |

(52) U.S. Cl.
CPC ............. *A61K 47/186* (2013.01); *A61K 39/395* (2013.01); *A61K 39/39591* (2013.01); *A61K 47/18* (2013.01); *C07K 16/22* (2013.01); *C07K 16/241* (2013.01); *C07K 16/2887* (2013.01); *A61K 9/0019* (2013.01)

(58) Field of Classification Search
None
See application file for complete search history.

(56) References Cited

U.S. PATENT DOCUMENTS

| | | |
|---|---|---|
| 4,399,216 A | 8/1983 | Axel et al. |
| 4,676,980 A | 6/1987 | Segal et al. |
| 4,816,567 A | 3/1989 | Cabilly et al. |
| 4,975,278 A | 12/1990 | Senter et al. |
| 5,078,997 A | 1/1992 | Hora et al. |
| 5,500,362 A | 3/1996 | Robinson et al. |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,661,016 A | 8/1997 | Lonberg et al. |
| 5,821,337 A | 10/1998 | Carter et al. |
| 7,390,786 B2 | 6/2008 | Warne et al. |
| 7,666,413 B2 | 2/2010 | Liu et al. |
| 7,758,860 B2 | 7/2010 | Warne et al. |
| 2002/0045571 A1 | 4/2002 | Liu et al. |
| 2004/0033228 A1 | 2/2004 | Krause et al. |
| 2004/0197324 A1 | 10/2004 | Liu et al. |
| 2005/0175603 A1 | 8/2005 | Liu et al. |
| 2006/0088523 A1 | 4/2006 | Andya et al. |
| 2006/0127395 A1 | 6/2006 | Arvinte et al. |
| 2007/0116700 A1 | 5/2007 | Liu et al. |
| 2008/0085263 A1 | 4/2008 | Thuresson et al. |
| 2008/0160014 A1 | 7/2008 | Warne et al. |
| 2008/0200383 A1 | 8/2008 | Jennings et al. |
| 2008/0267959 A1 | 10/2008 | Campbell et al. |
| 2009/0259023 A1 | 10/2009 | Su et al. |
| 2010/0158908 A1 | 6/2010 | Rehder et al. |
| 2010/0239567 A1 | 9/2010 | Esue |
| 2011/0318343 A1 | 12/2011 | Kaisheva et al. |
| 2012/0076783 A1 | 3/2012 | Liu et al. |

FOREIGN PATENT DOCUMENTS

| | | |
|---|---|---|
| AU | 2010-200784 A1 | 3/2010 |
| EP | 0 125 023 A1 | 11/1984 |

(Continued)

OTHER PUBLICATIONS

Du et al., Biotechnology and Bioengineering (2011) 108(3), 632-636.*

(Continued)

*Primary Examiner* — Marcela M Cordero Garcia
*Assistant Examiner* — Catherine Mader
(74) *Attorney, Agent, or Firm* — Oliff PLC

(57) ABSTRACT

A process of lowering the viscosity of a solution includes preparing a solution comprising a compound of formula I, at a concentration in the final formulation of between 10 and 250 mM, and a protein having at least one antibody fragment whose concentration is between 50 and 350 mg/mL and whose pH is between 5 and 8.

Formula I

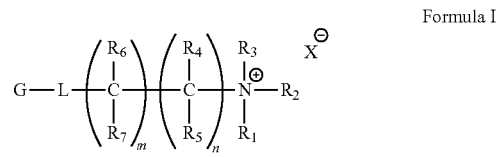

The compound lowers the viscosity of the solution, which is difficult to inject, by a value of at least 15% relative to the viscosity of a solution of at least one protein having at least one antibody fragment of the same concentration and of the same pH not containing the compound.

30 Claims, No Drawings

(56) References Cited

FOREIGN PATENT DOCUMENTS

| | | |
|---|---|---|
| EP | 0 173 494 A3 | 3/1986 |
| EP | 0 308 936 A2 | 3/1989 |
| EP | 0 404 097 A2 | 12/1990 |
| EP | 0 661 060 A2 | 7/1995 |
| EP | 1 688 432 A1 | 8/2006 |
| EP | 1 977 763 A1 | 10/2008 |
| EP | 1 324 776 B1 | 9/2009 |
| EP | 1 610 820 B1 | 9/2010 |
| EP | 2 335 725 A1 | 6/2011 |
| EP | 2 596 796 A1 | 5/2013 |
| JP | A-2006-511457 | 4/2006 |
| JP | A-2006-514954 | 5/2006 |
| JP | A-2008-520551 | 6/2008 |
| JP | A-2010-159273 | 7/2010 |
| JP | A-2011-184446 | 9/2011 |
| WO | WO 81/01145 A1 | 4/1981 |
| WO | WO 88/07378 A1 | 10/1988 |
| WO | WO 89/05859 A1 | 6/1989 |
| WO | WO 91/00360 A1 | 1/1991 |
| WO | WO 92/00373 A1 | 1/1992 |
| WO | WO 93/08829 A1 | 5/1993 |
| WO | WO 93/11161 A1 | 6/1993 |
| WO | WO 94/04690 A1 | 3/1994 |
| WO | WO 96/27011 A1 | 9/1996 |
| WO | WO 97/04801 A1 | 2/1997 |
| WO | WO 99/01556 A2 | 1/1999 |
| WO | WO 02/30463 A2 | 4/2002 |
| WO | WO 02/45686 A2 | 6/2002 |
| WO | WO 02/096457 A2 | 12/2002 |
| WO | WO 2004/060343 A1 | 7/2004 |
| WO | WO 2004/091658 A1 | 10/2004 |
| WO | WO 2005/035574 A1 | 4/2005 |
| WO | WO 2005/072772 A1 | 8/2005 |
| WO | WO 2006/012500 A2 | 2/2006 |
| WO | WO 2006/065746 A2 | 6/2006 |
| WO | WO 2006/116269 A2 | 11/2006 |
| WO | WO 2007/037795 A2 | 4/2007 |
| WO | WO 2007/076062 A2 | 7/2007 |
| WO | WO 2009/043049 A2 | 4/2009 |
| WO | WO 2011/017330 A1 | 2/2011 |
| WO | WO 2011/104381 A2 | 9/2011 |
| WO | WO 2011/109415 A2 | 9/2011 |
| WO | WO 2011/139718 A1 | 11/2011 |
| WO | WO 2011/143307 A1 | 11/2011 |
| WO | WO 2012/138958 A1 | 10/2012 |
| WO | WO 2012/141978 A2 | 10/2012 |
| WO | WO 2013/028334 A2 | 2/2013 |
| WO | WO 2013/063510 A1 | 5/2013 |

OTHER PUBLICATIONS

Connolly et al., "Weak Interactions Govern the Viscosity of Concentrated Antibody Solutions: High-Throughput Analysis Using the Diffusion Interaction Parameter", *Biophysical Journal*, 2012, 103, 69-78.

Shire, "Formulation and manufacturability of biologics," *Current Opinion in Biotechnology*, 2009, 20, 708-714.

Cilurzo et al., "Injectability Evaluation: An Open Issue," *AAPS PharmSciTech*, 2011, 12(2), 604-609.

Saluja & Kalonia, "Nature and consequences of protein-protein interactions in high protein concentration solutions," *International Journal of Pharmaceutics*, 2008, 358, 1-15.

Shire et al., "Challenges in the Development of High Protein Concentration Formulations," *Journal of Pharmaceutical Sciences*, 2004, 93(6), 1390-1402.

Guo et al., "Structure-Activity Relationship for Hydrophobic Salts at Viscosity-Lowering Excipients for Concentrated Solutions of Monoclonal Antibodies," *Pharm Res*, 2012.

Galush et al., "Viscosity Behavior of High-Concentration Protein Mixtures," *Journal of Pharmaceutical Sciences*, 2012, 101(3), 1012-20.

Frokjaer & Otzen, "Protein Drug Stability: a formulation challenge," *Nat Rev Drug Discov*, 2005, 4, 298-306.

Morrison et al., "Chimeric human antibody molecules: mouse antigen-binding domains with human constant region domains," *Proc. Natl. Acad. Sci. USA*, 1984, 81, pp. 6851-6855.

Neuberger et al., "Recombinant antibodies possessing novel effector functions," 1984, *Nature*, 312, 604-8.

Du & Klibanov, "Hydrophobic Salts Markedly Diminish Viscosity of Concentrated Protein Solutions," *Biotechnol Bioeng*, 2011, 108(3), 632-636.

Adler; "Challenges in the Development of Pre-filled Syringes for Biologics from a Formulation Scientist's Point of View;" *American Pharmaceutical Review*; Feb. 2012; vol. 15, No. 1.

Vincke et al.; "Introduction to Heavy Chain Antibodies and Derived Nanobodies;" *Single Domain Antibodies: Methods and Protocols, Methods in Molecular Biology*; 2012; pp. 15-26; vol. 911.

Wesolowski et al.; "Single domain antibodies: promising experimental and therapeutic tools in infection and immunity;" *Med. Microbiol Immunol*; 2009; pp. 157-174; vol. 198.

Kabat et la.; "Sequences of Proteins of Immunological Interest;" U.S. Department of Health and Human Services, *Public Health Service, National Institute of Health*; 1991; pp. xv; 5th Edition.

Holliger et al., "Diabodies: small bivalent and bispecific antibody fragments," *Proc. Natl. Acad. Sci.USA*, 1993, 90(4), 6444-48.

\* cited by examiner

PROCESS FOR LOWERING THE VISCOSITY OF HIGHLY CONCENTRATED PROTEIN SOLUTIONS

The invention relates to a process which consists in using viscosity-reducing compounds (identified hereinbelow as VR) for lowering the viscosity of solutions comprising at least one protein comprising at least one antibody fragment.

Monoclonal antibodies (mAbs) are a class of rapidly developing therapeutic proteins for treating serious pathologies such as certain cancers, infectious diseases and autoimmune diseases. To date, more than 20 mAbs have been approved by the FDA, and about 20% of the therapeutic proteins currently in development are antibodies.

Antibodies may be administered parenterally, such as intravenous (IV), subcutaneous (SC) or intramuscular (IM) injection. The SC and IM routes make it possible to reduce the cost of the treatments and improve the patient comfort.

For SC and IM injections, the small volume that may be injected (0.5-2 mL) imposes the development of concentrated antibody formulations since the required doses are conventionally 100 mg to 1 g in order to achieve a therapeutic effect. At concentrations above 100 mg/mL, the mAbs solutions are often unstable and viscous, making the manufacturing steps (purification, concentration and distribution steps) difficult, as is described in the publication by Shire, *Current Opinion in Biotechnology* 2009, 20, 708-714.

The viscosity of the formulations entails injectability problems and makes the administrations painful to the patient, as is described in the publication by Cilurzo et al., *AAPS PharmSciTech*, 2011, 12(2), 604-609.

This viscosity of concentrated protein formulations thus becomes a veritable challenge, as is described in the publication by Adler, *American Pharmaceutical Review*, February 2012, 15(1).

Even though the factors governing these viscosity increases are quite poorly described and identified, many publications show that the increase in viscosity of highly concentrated antibody solutions results from at least two factors: steric effects (volume exclusion) and protein-protein interactions, as is described in the publication by Saluja & Kalonia, *Int J Pharm*, 2008, 358(1-2), 1-15.

However, as the only factor that is able to be modified by the formulator is the viscosity of the solutions, since the other factors, namely the doses and the caliber of the needles, cannot be modified in the majority of cases, the need to identify viscosity-reducing excipients that are capable of lowering the viscosity of highly concentrated protein solutions has become crucial and strategic in the pharmaceutical industry.

The use of a salt such as NaCl has been described especially in the publication by Shire et al. *J Pharm Sci* 2004, 93(6), 1390-402 or U.S. Pat. No. 7,666,413 as making it possible to lower the viscosity of concentrated mAb solutions. However, this solution is not universal, and the viscosity of many mAb formulations is not reduced or insufficiently reduced by the addition of a salt such as NaCl, as is confirmed in the publication by Guo et al., *Pharm Res*, 2012, 29(11), 3102-3109.

It has also been reported in the publication by Guo et al., Pharm Res, 2012, 29(11), 3102-3109 that certain hydrophobic anions make it possible to reduce the viscosity of concentrated mAb solutions, and the best candidates were defined in the conclusions of the structure-activity study presented as needing to be hydrophobic, bulky and aliphatic. However, these salts must be used at concentrations of at least 250 mM in order to achieve their optimal activity.

Amino acids (U.S. Pat. No. 7,666,413) and amino acid derivatives (patent application WO 2011/139 718) have also been described as making it possible to reduce the viscosity of formulations containing an active protein of mAb type. In particular, the arginine hydrochloride salt, which is a compound commonly used in protein purification and formulation processes, see for example the publication by Frokjaer S., *Nat Rev Drug Discov* 2005, 4(4), 298-306, may be considered as one of the references for assessing the lowering of viscosity. To do this, the arginine hydrochloride salt is commonly used at a concentration of about 200 mM, as is reported in U.S. Pat. No. 7,666,413 or the publication by Galush et al., J Pharm Sci 2012, 101(3), 1012-20.

Patent applications WO 2012/138 958 and WO 2012/141 978 describe a method for reducing the viscosity of a formulation containing a therapeutic polypeptide and citrate (WO 2012/138 958) or acetate (WO 2012/141 978), the method consisting in adding to said formulation one or more amino acids. These patent applications especially illustrate the uses of phenylalanine and of tyrosine for lowering the viscosity of solutions of anti-IL5 or anti-ELR antibodies. However, in patent application WO 2012/141 978, it is demonstrated in an example that tyrosine (0.004% w/v, i.e. 0.2 mM) increases the viscosity of the anti-IL5 antibody solution (+44% increase).

Patent application WO 2013/063 510 describes a pharmaceutically stable formulation comprising one or more amino acids for stabilizing a protein of the formulation, and one or more amino acids for reducing the viscosity of the formulation. However, it is demonstrated in an example that phenylalanine (0.2%, i.e. 12 mM) increases, on the contrary, the viscosity of a trastuzumab formulation at 300 mg/mL (+83% increase).

The Applicant has, surprisingly, identified compounds bearing a phenyl group and an ammonium group which are capable of appreciably reducing the viscosity of solutions, which are difficult to inject, of at least one protein comprising at least one antibody fragment.

The invention thus relates to the use of a compound of formula I, at a concentration in the final formulation of between 10 and 250 mM:

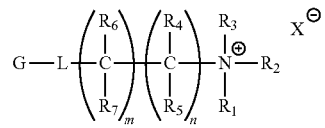

Formula I in which:
G is a C6 to C10 phenyl or alkylphenyl group, the phenyl group possibly being substituted with one or more hydroxyl groups, L is either a bond or a function chosen from the group consisting of the ether function, the carbamate function and the amide function, m and n are identical or different integers between 0 and 2 such that $0 < m+n \leq 3$, $R_1$, $R_2$ and $R_3$, which may be identical or different, are either a hydrogen atom or a chain comprising 1 to 4 carbon atoms, said chain possibly comprising one or more N or O heteroatoms, $R_4$, $R_5$, $R_6$ and $R_7$, which may be identical or different, are either a hydrogen atom or a chain comprising 1 to 6 carbon atoms, said chain possibly comprising one or more N or O heteroatoms, but does not bear any carboxylic acid functions, X⁻ is an anion chosen from the group consisting of halides, carboxylates, sulfates, phosphates and sulfonates, the asymmetric carbon atoms have an R or S configuration, said compound having a solubility in water of at least 20 mM at a pH of between 5 and 8, to lower the viscosity of a solution, which is difficult to inject, of at least one protein comprising at least one antibody fragment whose concentration is between 50 and 350 mg/mL and whose pH is between 5 and 8, by a value of at least 15% relative to the viscosity of a solution of at least one protein comprising at least one antibody fragment of the same concentration and of the same pH not containing said compound.

The term "solution, which is difficult to inject, of at least one protein comprising at least one antibody fragment" means a solution of at least one protein comprising at least one antibody fragment whose viscosity is at least 15 cP. It is generally accepted that such a solution whose viscosity is at least 15 cP is difficult to inject subcutaneously using a needle of a caliber of at least 29 G. The Applicant has adopted as the limiting caliber at least 29 G, since the latter is the upper caliber admissible for the injection comfort not to be too degraded.

The term "protein comprising at feast one antibody fragment" means a protein chosen from monoclonal antibodies (mAbs), polyclonal antibodies, fusion proteins, nanobodies, bispecific antibodies and antibodies coupled to cytotoxic active principles (ADC).

The term "monoclonal antibody" means a "whole antibody", an "antibody fragment" or an "antibody derivative" which has an identical and unique specificity, i.e. which recognizes only one type of epitope on a given antigen.

According to the present invention, an antibody may also be referred to as an immunoglobulin.

The term "whole antibody" means an antibody composed of two identical heavy chains ("HC") and two identical light chains ("LC") which are linked via a disulfide bridge. Each chain consists, in the N-terminal position, of a variable region (or domain) (encoded by the rearranged genes V-J for the light chains and V-D-J for the heavy chains) which is specific for the antigen against which the antibody is directed, and, in the C-terminal position, of a constant region, consisting of a single LC domain for the light chains or of several domains for the heavy chains. This variable region comprises three segments known as "complementarity-determining regions" ("CDRs") or "hypervariable regions", which are mainly responsible for the binding to the epitope of an antigen. The two heavy chains (H, heavy) and the two light chains (L, light) are mutually identical. The light chain is composed of two domains, a variable domain V and a constant domain C, which are folded independently of each other in space. They are referred to as VL and CL. The heavy chain also comprises a domain V, noted VH, and three or four domains C, noted $CH^1$ to $CH^4$. Each domain comprises about 110 amino acids and is structured in a comparable manner. The two heavy chains are linked via disulfide bridges and each heavy chain is linked to a light chain also via a disulfide bridge. The region which determines the specificity of the antibody for the antigen is borne by the variable parts, whereas the constant parts may interact with the Fc receptors of the effector cells or molecules like the complement to mediate various functional properties. The term "VH" refers to the variable regions of a heavy immunoglobulin chain of an antibody, including the heavy chains of a fragment Fv, scFv, dsFv, Fab, Fab' or F(ab)'. The term "VL" refers to the variable regions of a light immunoglobulin chain of an antibody, including the light chains of a fragment Fv, scFv, dsFv, Fab, Fab' or F(ab)'. The term "CDR or CDRs regions" denotes the hypervariable regions of the heavy and light chains of immunoglobulins as defined by Kabat et al. (Kabat et al., Sequences of proteins of immunological interest, 5th Ed., U.S. Department of Health and Human Services, NIH, 1991, and later editions, XV). Three heavy-chain CDRs and three light-chain CDRs exist. The term CDR or CDRs is used herein to denote, depending on the case, one or more of these regions, or even all of these regions, which contain the majority of the amino acid residues responsible for the affine binding of the antibody to the antigen or the epitope it recognizes. The most conserved regions of the variable domains are known as the FR (for "framework") regions or sequences, of which there are four (FR1 to FR4).

Antibodies are subdivided into five classes or isotypes: IgG, IgA, IgM, IgE and IgD, according to the structure of the constant domains of the heavy chains, i.e. respectively, chains γ, α, β, ε and δ.

The IgG and IgA classes are moreover subdivided into subclasses depending especially on the size of the hinge regions and also on the number and position of the disulfide bridges between heavy chains.

The IgG class is subdivided into four subclasses, i.e. IgG1, IgG2, IgG3 and IgG4.

The IgA class is, itself, subdivided into two subclasses, i.e. IgA1 and IgA2.

In one embodiment of the use or of the process, the protein comprising at least one antibody fragment is a monoclonal antibody.

In one embodiment of the use or of the process, the monoclonal antibody is an IgG.

In one embodiment of the use or of the process, the monoclonal antibody is an IgA.

In one embodiment of the use or of the process, the monoclonal antibody is an IgM.

In one embodiment of the use or of the process, the monoclonal antibody is an IgE.

In one embodiment of the use or of the process, the monoclonal antibody is an IgD.

In one embodiment of the use or of the process, the monoclonal antibody is an IgG1.

In one embodiment of the use or of the process, the monoclonal antibody is an IgG2.

In one embodiment of the use or of the process, the monoclonal antibody is an IgG3.

In one embodiment of the use or of the process, the monoclonal antibody is an IgG4.

In one embodiment of the use or of the process, the monoclonal antibody is an IgA1.

In one embodiment of the use or of the process, the monoclonal antibody is an IgA2.

The term "antibody fragment" means any functional antibody fragment, e.g. Fab (antigen-binding fragment), Fv, scFv (single-chain Fv), Fc (crystallizable fragment), F(ab')2, Fab', scFv-Fc, synthetic polypeptides containing sequences of one or more CDRs, which generally have the same binding specificity as the antibody from which they are derived.

According to the present invention, the antibody fragments of the invention may be obtained from antibodies via methods such as digestion with enzymes, such as pepsin or papain and/or by cleavage of the disulfide bridges via chemical reduction. The enzymatic digestion of antibodies with papain generates two identical fragments, known as "Fab fragment" (antigen-binding fragment), and an Fc fragment (crystallizable fragment). The Fc fragment is the support for the effector functions of the immunoglobulins. By digestion with pepsin, a fragment F(ab')2 is generated, in which the two Fab fragments remain linked via two disulfide bridges, and the Fc fragment is cleaved into several peptides. The fragment F(ab')2 is formed from two Fab' fragments, linked via intercatenary disulfide bridges to form an F(ab')2.

Thus, since the "monoclonal antibody" according to the invention may advantageously contain one or more of these fragments, all the combinations between the fragments mentioned previously form part of the invention.

The term "antibody derivative" means any antibody, this antibody possibly comprising one or more mutations, substitutions, deletions and/or additions of one or more amino acid residues. Such an addition, substitution or deletion may be located on any position of the molecule. In the case where several amino acids have been added, substituted or deleted, any combination of addition, substitution or deletion may be considered, provided that the resulting antibody always has at least the advantageous properties of the antibody of the invention.

According to the invention, the "monoclonal antibody" may advantageously be a "chimeric antibody" or a "humanized antibody". The term "chimeric antibody" means an antibody in which the variable regions of the light and heavy chains, or at least one domain or fragment of these regions, belong to a species that is different from the constant regions of the light chains and of the heavy chains. The term "humanized antibody" means an antibody which mainly contains human immunoglobulin sequences. This term generally makes reference to a nonhuman immunoglobulin which has been modified by incorporation of human sequences or of residues found in human sequences.

The antibodies according to the invention may be constituted by using the standard techniques for recombinant DNA, well known to those skilled in the art, for example by using the techniques for the construction of "chimeric" antibodies described, for example, in Morrison et al., *Proc. Natl. Acad. Sci. U.S.A.*, 1984, 81(21), pp. 6851-55, in which the recombinant DNA technology is used to replace the constant region of a heavy chain and/or the constant region of a light chain of an antibody originating from a nonhuman mammal with the corresponding regions of a human immunoglobulin. Such antibodies and their method of preparation are also described in patent application EP 173 494, in the document by Neuberger, M. S. et al., *Nature* 312 (5995): 604-8 (1985), and also in document EP 125 023, for example. Methods for generating chimeric antibodies are widely available to those skilled in the art. For example, the heavy and light chains of the antibody may be expressed separately by using a vector for each chain, or alternatively may be integrated into a single vector.

By way of example, among the commercialized monoclonal antibodies, mention will be made of the following monoclonal antibodies: muromonab-CD3 (sold under the name Orthoclone Okt3®), abciximab (sold under the name Reopro®), rituximab (sold under the names MabThera® and Rituxan®), basiliximab (sold under the name Simulect®), daclizumab (sold under the name Zenapax®), palivizumab (sold under the name Synagis®), infliximab (sold under the name Remicade®), trastuzumab (sold under the name Herceptin®), alemtuzumab (sold under the names MabCampath®, Campath-1H®), adalimumab (sold under the name Humira®), tositumomab-I131 (sold under the name Bexxar®), efalizumab (sold under the name Raptiva®), cetuximab (sold under the name Erbitux®), omalizumab (sold under the name Xolair®), bevacizumab (sold under the name Avastin®), natalizumab (sold under the name Tysabri®), ranibizumab (sold under the name Lucentis®), panitumumab (sold under the name Vectibix®), eculizumab (sold under the name Soliris®), golimumab (sold under the name Simponi®), canakinumab (sold under the name Ilaris®), catumaxomab (sold under the name Removab®), ustekinumab (sold under the name Stelara®), tocilizumab (sold under the names RoActemra® and Actemra®), ofatumumab (sold under the name Arzerra®), denosumab (sold under the name Prolia®), belimumab (sold under the name Benlysta®), raxibacumab (not yet sold), ipilimumab (sold under the name Yervoy®), certolizumab pegol (sold under the name Cimzia®), ibritumomab tiuxetan (sold under the name Zevalin®) and pertuzumab (sold under the name Perjeta®).

The term "polyclonal antibody" means a mixture of "whole antibodies", a mixture of "antibody fragments" or a mixture of "antibody derivatives" which recognize different types of epitope on a given antigen.

In one embodiment of the use or of the process, the protein comprising at least one antibody fragment is a polyclonal antibody.

The term "fusion protein" means a construct which contains several proteins or polypeptides of different origin. This fusion protein is encoded by a nucleic acid obtained via recombinant DNA techniques that are well known to those skilled in the art. According to the present invention, the fusion protein consists of a "monoclonal antibody" fragment as described previously and a fragment of a "protein of interest".

In one embodiment of the use or of the process, the protein comprising at least one antibody fragment is a fusion protein.

By way of example, mention will be made of the fusion protein consisting of a monoclonal antibody fragment which is the Fc region of an immunoglobulin IgG1 and a fragment of a protein of interest which is the extracellular domain of the receptor of protein CTLA-4 (Cytotoxic T-Lymphocyte Antigen 4), this fusion protein i.e. abatacept, being sold under the name Orencia®.

By way of example, mention will also be made of the fusion protein consisting of a monoclonal antibody fragment which is the Fc region of an IgG1 and a fragment of a protein of interest which is the P75 fraction of the soluble receptor of TNF-alpha, this fusion protein, i.e. etanercept being sold under the name Enbrel®.

By way of example, mention will also be made of the fusion protein consisting of a monoclonal antibody fragment which is the Fc region of an IgG1 and a fragment of a protein of interest which are the extracellular portions of IL-1R1 (interleukin-1 receptor component) and of IL-1RAcP (IL-1 receptor accessory protein), this fusion protein, i.e. arcalyst, being sold under the name Rilonacept®.

By way of example, mention will also be made of the fusion protein consisting of a monoclonal antibody fragment, which are the regions IgG1 hinge, C(H)2 and C(H)3 domains, and a fragment of a protein of interest which is the extracellular domain of LFA-3, this fusion protein, i.e. amevive, being sold under the name Alefacept®.

The term "nanobody" means any single variable domain of heavy immunoglobulin chains. Nanobodies are more widely described in the publication by C. Vincke and S. Muyldermans in D. Saerens and S. Muyldermans (eds.) *Single Domain Antibodies: Methods and Protocols*, Methods in Molecular Biology, vol. 911; Springer Science+Business Media, LLC, 2012, 15-26 and Wesolowski et al., Med Microbiol Immunol (2009), 198(3), 157-174.

In one embodiment of the use or of the process, the protein comprising at least one antibody fragment is a nanobody.

The term "bispecific antibody" (also known as a "bifunctional antibody" or a "diabody") means any immunoglobulin fragment comprising two sites of presentation to the antigen.

Bifunctional antibodies are more widely described in the publication by Hollinger et al., *Proc. Natl. Acad. Sci. USA* 90(4): 6444-6448 (1993).

In one embodiment of the use or of the process, the protein comprising at least one antibody fragment is a bispecific antibody.

The term "antibody coupled to a cytotoxic active principle" means a "monoclonal antibody" as described previously coupled to a cytotoxic active principle.

As examples of cytotoxic active principles, mention will be made especially of ozogamicin and vedotin.

In one embodiment of the use or of the process, the protein comprising at least one antibody fragment is an antibody coupled to a cytotoxic active principle.

By way of example, the antibody coupled to a cytotoxic active principle is the antibody brentuximab coupled to the cytotoxic active principle vedotin. This antibody coupled to this cytotoxic active principle is sold under the name Adcetris®.

In one embodiment, the invention also relates to the use of a compound of formula I, at a concentration in the final formulation of between 10 and 250 mM, for lowering the viscosity of a solution, which is difficult to inject, of at least one protein comprising at least one antibody fragment whose concentration is between 50 and 350 mg/mL and whose pH is between 5 and 8, by a value of at least 15% relative to the viscosity of a solution of at least one protein comprising at least one antibody fragment of the same concentration and of the same pH not containing said compound.

In one embodiment, the invention also relates to the use of a compound of formula I, at a concentration in the final formulation of between 10 and 250 mM, for lowering the viscosity of a solution, which is difficult to inject, of at least one protein comprising at least one antibody fragment whose concentration is between 50 and 350 mg/mL and whose pH is between 5 and 8, by a value of between 15% and 95% relative to the viscosity of a solution of at least one protein comprising at least one antibody fragment of the same concentration and of the same pH not containing said compound.

In one embodiment, the invention also relates to the use of a compound of formula I, at a concentration in the final formulation of between 100 and 200 mM, for lowering the viscosity of a solution, which is difficult to inject, of at least one protein comprising at least one antibody fragment whose concentration is between 50 and 350 mg/mL and whose pH is between 5 and 8, by a value of at least 15% relative to the viscosity of a solution of at least one protein comprising at least one antibody fragment of the same concentration and of the same pH not containing said compound.

In one embodiment, the invention also relates to the use of a compound of formula I, at a concentration in the final formulation of between 100 and 200 mM, for lowering the viscosity of a solution, which is difficult to inject, of at least one protein comprising at least one antibody fragment whose concentration is between 50 and 350 mg/mL and whose pH is between 5 and 8, by a value of between 15% and 95% relative to the viscosity of a solution of at least one protein comprising at least one antibody fragment of the same concentration and of the same pH not containing said compound.

The invention also relates to the process for lowering the viscosity, which consists in preparing a solution comprising a compound of formula I and a protein comprising at least one antibody fragment whose concentration is between 50 and 350 mg/mL and whose pH is between 5 and 8.

In one embodiment, the process according to the invention is characterized in that a solution is prepared comprising a compound of formula I and a protein comprising at least one antibody fragment whose concentration is between 50 and 350 mg/mL and whose pH is between 5 and 8, for lowering the viscosity of this solution by a value of at least 15% relative to the viscosity of a solution of at least one protein comprising at least one antibody fragment of the same concentration and of the same pH not containing said compound.

In one embodiment, the process according to the invention is characterized in that a solution is prepared comprising a compound of formula I and a protein comprising at least one antibody fragment whose concentration is between 50 and 350 mg/mL and whose pH is between 5 and 8, for lowering the viscosity of this solution by a value of between 15% and 95% relative to the viscosity of a solution of at least one protein comprising at least one antibody fragment of the same concentration and of the same pH not containing said compound.

In one embodiment, the process according to the invention is characterized in that the final solution has a concentration of compound of formula I of between 10 and 250 mM.

In one embodiment, the process according to the invention is characterized in that the final solution has a concentration of compound of formula I of between 100 and 200 mM.

In one embodiment, G is a phenyl group.

In one embodiment, G is a phenyl group substituted with one or more hydroxyl groups.

In one embodiment, $R_4$ and $R_6$, which may be identical or different, are either a hydrogen atom or a chain comprising 1 to 6 carbon atoms, said chain possibly comprising one or more functions chosen from the group consisting of hydroxyl, amide and ester functions.

In one embodiment, $R_5$ and $R_7$, which may be identical or different, are either a hydrogen atom or a chain comprising 1 to 6 carbon atoms, said chain possibly comprising one or more functions chosen from the group consisting of hydroxyl, amide and ester functions.

In one embodiment, at least one group $R_4$, $R_5$, $R_6$ or $R_7$ is not a hydrogen atom, and comprises an amine N-oxide function.

In one embodiment, at least one group $R_4$, $R_5$, $R_6$ or $R_7$ is not a hydrogen atom, and comprises an amine N-oxide function and an amide function.

In one embodiment, the amine N-oxide functions are salified, for example in hydrochloride salt form:

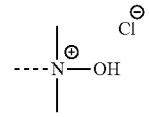

It has been chosen to represent the ammonium functions in the form "$NR_4^+ \cdot X^-$"; however, it is obvious that, when at least one of the groups R is a hydrogen atom, 100% of the species present are not necessarily in this form under certain pH conditions. In the pH range 5 to 8 selected in the invention, it is possible that some of the species present are not in salt form at a given pH.

In one embodiment of the use or of the process, the pH is between 5 and 6.5.

In one embodiment of the use or of the process, the pH is between 5.5 and 6.5.

In one embodiment of the use or of the process, the pH is between 6 and 8.

In one embodiment of the use or of the process, the pH is between 6 and 7.5.

In one embodiment of the use or of the process, the pH is between 6 and 7.

A concentration expressed in M is a concentration in mol/L.

A concentration expressed in mM is a concentration in mmol/L.

In one embodiment of the use or of the process, the concentration of the compound of formula I in the final formulation is between 10 and 200 mM.

In one embodiment of the use or of the process, the concentration of the compound of formula I in the final formulation is between 25 and 200 mM.

In one embodiment of the use or of the process, the concentration of the compound of formula I in the final formulation is between 50 and 200 mM.

In one embodiment of the use or of the process, the concentration of the compound of formula I in the final formulation is between 50 and 175 mM.

In one embodiment of the use or of the process, the concentration of the compound of formula I in the final formulation is between 100 and 250 mM.

In one embodiment of the use or of the process, the concentration of the compound of formula I in the final formulation is between 100 and 200 mM.

In one embodiment of the use or of the process, the concentration of the compound of formula I in the final formulation is between 100 and 175 mM.

In one embodiment of the use or of the process, the concentration of protein comprising at least one antibody fragment in the final formulation is between 100 and 350 mg/mL.

In one embodiment of the use or of the process, the concentration of protein comprising at least one antibody fragment in the final formulation is between 100 and 300 mg/mL.

In one embodiment of the use or of the process, the concentration of protein comprising at least one antibody fragment in the final formulation is between 100 and 250 mg/mL.

In one embodiment of the use or of the process, the concentration of protein comprising at least one antibody fragment in the final formulation is between 150 and 300 mg/mL.

In one embodiment of the use or of the process, the concentration of protein comprising at least one antibody fragment in the final formulation is between 150 and 250 mg/mL.

In one embodiment of the use or of the process, the viscosity is lowered by a value of at least 15%.

In one embodiment of the use or of the process, the viscosity is lowered by a value of between 15% and 95%.

In one embodiment of the use or of the process, the viscosity is lowered by a value of between 15% and 90%.

In one embodiment of the use or of the process, the viscosity is lowered by a value of between 20% and 80%.

In one embodiment of the use or of the process, the viscosity is lowered by a value of between 30% and 70%.

In one embodiment of the use or of the process, the viscosity is lowered by a value of between 35% and 65%.

In one embodiment of the use or of the process, the viscosity is lowered by a value of between 30% and 65%.

In one embodiment of the use or of the process, the viscosity is lowered by a value of between 25% and 65%.

In one embodiment of the use or of the process, the viscosity is lowered by a value of between 20% and 65%.

In one embodiment of the use or of the process, the compound of formula I is chosen from compounds in which the anion $X^-$ is a carboxylate chosen from the group consisting of acetates, succinates and citrates.

In one embodiment of the use or of the process, the compound of formula I is chosen from compounds in which the anion $X^-$ is chosen from the group of halides.

In one embodiment of the use or of the process, the compound of formula I is chosen from compounds in which the anion $X^-$ is a hydrochloride.

In one embodiment of the use or of the process, the compound is chosen from compounds of formula I in which the groups $R_1$, $R_2$ and $R_3$, which may be identical or different, are not a hydrogen atom.

In one embodiment, the groups $R_1$, $R_2$ and $R_3$, which may be identical or different, are chosen from the group consisting of a hydrogen atom, methyl, ethyl, propyl, n-butyl, sec-butyl, isobutyl, 2-hydroxyethyl, 3-hydroxypropyl, 4-hydroxybutyl and 1-methoxypropyl.

In one embodiment, $R_1=R_2=R_3=H$.

In one embodiment, $R_1=R_2=R_3=CH_3$.

In one embodiment, $R_1=R_2=H$ and $R_3=CH_2CH_2OH$.

In one embodiment of the use or of the process, the compound is chosen from the compounds of formula II:

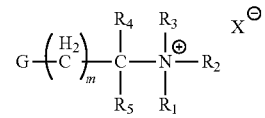

Formula II in which:
G is a C6 to C10 phenyl or alkylphenyl group, the phenyl group possibly being substituted with one or more hydroxyl groups, m is an integer equal to 0 or 1, $R_1$, $R_2$ and $R_3$, which may be identical or different, are either a hydrogen atom or a chain comprising 1 to 4 carbon atoms, said chain possibly comprising one or more heteroatoms N or O, $R_4$ is a chain comprising from 1 to 6 carbon atoms, said chain possibly comprising one or more heteroatoms N or O, but does not comprise any carboxylic acid functions, $R_5$ is either a hydrogen atom or a chain comprising 1 to 6 carbon atoms, said chain possibly comprising one or more heteroatoms N or O, but does not comprise any carboxylic acid functions, $X^-$ is an anion chosen from the group consisting of halides, carboxylates, sulfates, phosphates and sulfonates, the asymmetric carbon atoms have an R or S configuration.

In one embodiment, G is a phenyl group.

In one embodiment, G is a phenyl group substituted with one or more hydroxyl groups.

In one embodiment, $R_4$ is either a hydrogen atom or a chain comprising 1 to 6 carbon atoms, said chain possibly comprising one or more functions chosen from the group consisting of hydroxyl, amide and ester functions.

In one embodiment, $R_4$ is a chain comprising 1 to 6 carbon atoms, said chain possibly comprising one or more functions chosen from the group consisting of hydroxyl, amide and ester functions.

In one embodiment, $R_4$ is not a hydrogen atom, and comprises an amine N-oxide function.

In one embodiment, $R_4$ is not a hydrogen atom, and comprises an amine N-oxide function and an amide function.

In one embodiment, $R_5=H$ and $R_4=$

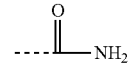

In one embodiment, $R_5$=H and $R_4$=CH$_2$OH

In one embodiment, $R_5$=H and $R_4$=

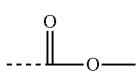

In one embodiment, $R_5$=H and $R_4$=

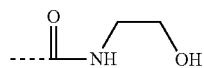

In one embodiment, $R_5$=H and $R_4$=

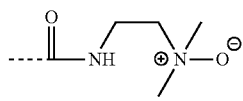

In one embodiment of the use or of the process, the compound is chosen from the compounds of formula IX:

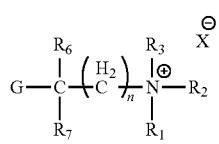

Formula IX in which:
- G is a C6 to C10 phenyl or alkylphenyl group, the phenyl group possibly being substituted with one or more hydroxyl groups,
- n is an integer equal to 1,
- $R_1$, $R_2$ and $R_3$, which may be identical or different, are either a hydrogen atom or a chain comprising 1 to 4 carbon atoms, said chain possibly comprising one or more heteroatoms N or O,
- $R_6$ is a chain comprising 1 to 6 carbon atoms, said chain possibly comprising one or more heteroatoms N or O, but does not comprise any carboxylic acid functions,
- $R_7$ is either a hydrogen atom or a chain comprising 1 to 6 carbon atoms, said chain possibly comprising one or more heteroatoms N or O, but does not comprise any carboxylic acid functions,
- $X^-$ is an anion chosen from the group consisting of halides, carboxylates, sulfates, phosphates and sulfonates,
- the asymmetric carbon atoms have an R or S configuration.

In one embodiment, G is a phenyl group.

In one embodiment, G is a phenyl group substituted with one or more hydroxyl groups.

In one embodiment, $R_6$ is either a hydrogen atom or a chain comprising 1 to 6 carbon atoms, said chain possibly comprising one or more functions chosen from the group consisting of hydroxyl, amide and ester functions.

In one embodiment, $R_6$ is a chain comprising 1 to 6 carbon atoms, said chain possibly comprising one or more functions chosen from the group consisting of hydroxyl, amide and ester functions.

In one embodiment, $R_6$ is not a hydrogen atom, and comprises an amine N-oxide function.

In one embodiment, $R_6$ is not a hydrogen atom, and comprises an amine N-oxide function and an amide function.

In one embodiment, $R_7$=H and $R_6$=

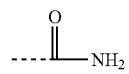

In one embodiment, $R_7$=H and $R_6$=—CH$_2$OH

In one embodiment, $R_7$=H and $R_6$=

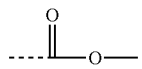

In one embodiment, $R_7$=H and $R_6$=

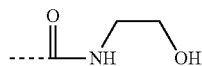

In one embodiment, $R_7$=H and $R_6$=

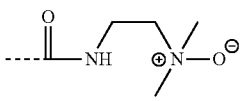

In one embodiment of the use or of the process, the compound is chosen from the compounds of formula III:

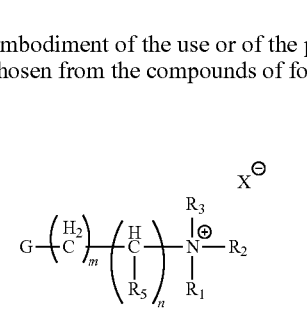

Formula III in which:
- G is a C6 to C10 phenyl or alkylphenyl group, the phenyl group possibly being substituted with one or more hydroxyl groups,
- m and n are integers, which may be identical or different, between 0 and 2 such that 0<m+n≤3,
- $R_1$, $R_2$ and $R_3$, which may be identical or different, are either a hydrogen atom or a chain comprising 1 to 4 carbon atoms, said chain possibly comprising one or more heteroatoms N or O,
- $R_5$ is either a hydrogen atom or an alkyl chain of 1 to 2 carbon atoms,
- $X^-$ is an anion chosen from the group consisting of halides, carboxylates, sulfates, phosphates and sulfonates,
- the asymmetric carbon atoms have an R or S configuration.

In one embodiment of the use or of the process, G is a C6 to C10 phenyl or alkylphenyl group in which the phenyl group is unsubstituted.

In one embodiment, G is a phenyl group.

In one embodiment, G is a phenyl group substituted with one or more hydroxyl groups.

In one embodiment of the use or of the process, the compound is chosen from the compounds of formula IV:

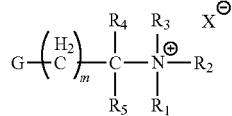

Formula IV in which:
- G is a C6 to C10 phenyl or alkylphenyl group, the phenyl group being substituted with one or more hydroxyl groups,
- m is an integer equal to 0 or 1,
- $R_1$, $R_2$ and $R_3$, which may be identical or different, are either a hydrogen atom or a chain comprising 1 to 4 carbon atoms, said chain possibly comprising one or more heteroatoms N or O,
- $R_4$ is a chain comprising 1 to 6 carbon atoms, said chain possibly comprising one or more heteroatoms N or O, but does not bear any carboxylic acid functions,
- $R_5$ is either a hydrogen atom or a chain comprising 1 to 6 carbon atoms, said chain possibly comprising one or more heteroatoms N or O, but does not bear any carboxylic acid functions,
- $X^-$ is an anion chosen from the group consisting of halides, carboxylates, sulfates, phosphates and sulfonates,
- the asymmetric carbon atoms have an R or S configuration.

In one embodiment, $R_4$ is either a hydrogen atom or a chain comprising 1 to 6 carbon atoms, said chain possibly comprising one or more functions chosen from the group consisting of hydroxyl, amide and ester functions.

In one embodiment, $R_4$ is a chain comprising 1 to 6 carbon atoms, said chain possibly comprising one or more functions chosen from the group consisting of hydroxyl, amide and ester functions.

In one embodiment, $R_4$ is not a hydrogen atom, and comprises an amine N-oxide function.

In one embodiment, at least one group $R_4$ is not a hydrogen atom, and comprises an amine N-oxide function and an amide function.

In one embodiment, $R_5$=H and $R_4$=

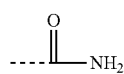

In one embodiment, $R_5$=H and $R_4$=—CH$_2$OH

In one embodiment, $R_5$=H and $R_4$=

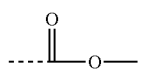

In one embodiment, $R_5$=H and $R_4$=

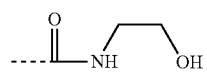

In one embodiment, $R_5$=H and $R_4$=

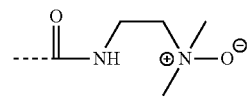

In one embodiment of the use or of the process, the compound is chosen from the compounds of formula V:

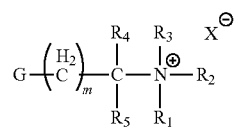

Formula V in which:
- G is a C6 to C10 phenyl or alkylphenyl group,
- m is an integer equal to 0 or 1,
- $R_1$, $R_2$ and $R_3$, which may be identical or different, are either a hydrogen atom or a chain comprising 1 to 4 carbon atoms, said chain possibly comprising one or more heteroatoms N or O,
- $R_4$ is a chain comprising 1 to 6 carbon atoms, said chain possibly comprising one or more heteroatoms N or O, but does not bear any carboxylic acid functions,
- $R_5$ is either a hydrogen atom or a chain comprising 1 to 6 carbon atoms, said chain possibly comprising one or more heteroatoms N or O, but does not bear any carboxylic acid functions,
- $X^-$ is an anion chosen from the group consisting of halides, acetates, sulfates, phosphates and sulfonates,
- the asymmetric carbon atoms have an R or S configuration.

In one embodiment, G is a phenyl group.

In one embodiment, $R_4$ is either a hydrogen atom or a chain comprising 1 to 6 carbon atoms, said chain possibly comprising one or more functions chosen from the group consisting of hydroxyl, amide and ester functions.

In one embodiment, $R_4$ is a chain comprising 1 to 6 carbon atoms, said chain possibly comprising one or more functions chosen from the group consisting of hydroxyl, amide and ester functions.

In one embodiment, $R_4$ is not a hydrogen atom, and comprises an amine N-oxide function.

In one embodiment, at least one group $R_4$ is not a hydrogen atom, and comprises an amine N-oxide function and an amide function.

In one embodiment, $R_5$=H and $R_4$=

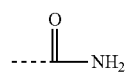

In one embodiment, $R_5$=H and $R_4$=—CH$_2$OH

In one embodiment, $R_5$=H and $R_4$=

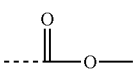

In one embodiment, $R_5$=H and $R_4$=

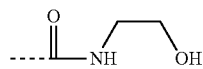

In one embodiment, $R_5$=H and $R_4$=

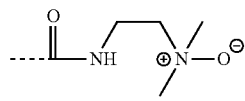

In one embodiment of the use or of the process, the compound is chosen from the compounds of formula XII:

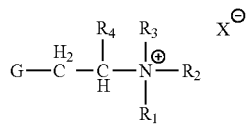

Formula XII in which:
- G is a C6 to C10 phenyl or alkylphenyl group, the phenyl group possibly being substituted with one or more hydroxyl groups,
- $R_1$, $R_2$ and $R_3$, which may be identical or different, are either a hydrogen atom or a chain comprising 1 to 4 carbon atoms, said chain possibly comprising one or more heteroatoms N or O,
- $R_4$ is a chain comprising 1 to 6 carbon atoms, said chain possibly comprising one or more heteroatoms N or O, but does not bear any carboxylic acid functions,
- $X^-$ is at least one anion chosen from the group consisting of halides, carboxylates, sulfates, phosphates and sulfonates, the asymmetric carbon atoms have an R or S configuration.

In one embodiment, G is a phenyl group.

In one embodiment, G is a phenyl group substituted with one or more hydroxyl groups.

In one embodiment, $R_4$ is a chain comprising 1 to 6 carbon atoms, said chain possibly comprising one or more functions chosen from the group consisting of hydroxyl, amide and ester functions.

In one embodiment, $R_4$ comprises an amine N-oxide function.

In one embodiment, $R_4$ comprises an amine N-oxide function and an amide function.

In one embodiment, $R_4$=

In one embodiment, $R_4$=—CH2OH

In one embodiment, $R_4$=

In one embodiment, $R_4$=

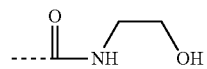

In one embodiment, $R_4$=

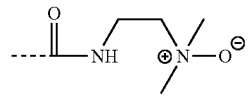

In one embodiment of the use or of the process, the compound is chosen from the compounds of formula XIII:

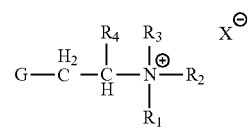

Formula XIII in which:
- G is a C6 to C10 phenyl or alkylphenyl group, the phenyl group possibly being substituted with one or more hydroxyl groups,
- $R_1$, $R_2$ and $R_3$, which may be identical or different, are either a hydrogen atom or a chain comprising 1 to 4 carbon atoms, said chain possibly comprising one or more heteroatoms N or O,
- $R_4$ is a chain comprising 1 to 6 carbon atoms, said chain comprising one or more heteroatoms N or O, an amine N-oxide function, but does not bear any carboxylic acid functions,
- $X^-$ is at least one anion chosen from the group consisting of halides, carboxylates, sulfates, phosphates and sulfonates, the asymmetric carbon atoms have an R or S configuration.

In one embodiment, G is a phenyl group.

In one embodiment, G is a phenyl group substituted with one or more hydroxyl groups.

In one embodiment, $R_4$ is a chain comprising 1 to 6 carbon atoms, said chain comprising an amine N-oxide function and possibly comprising one or more functions chosen from the group consisting of hydroxyl, amide and ester functions.

In one embodiment, $R_4$=

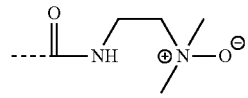

In one embodiment of the use or of the process, the compound is chosen from the compounds of formula XIV:

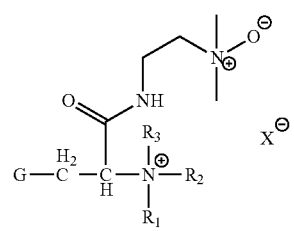

Formula XIV in which:
G is a C6 to C10 phenyl or alkylphenyl group, the phenyl group possibly being substituted with one or more hydroxyl groups,
$R_1$, $R_2$ and $R_3$, which may be identical or different, are either a hydrogen atom or a chain comprising 1 to 4 carbon atoms, said chain possibly comprising one or more heteroatoms N or O,
$X^-$ is at least one anion chosen from the group consisting of halides, carboxylates, sulfates, phosphates and sulfonates,
the asymmetric carbon atoms have an R or S configuration.

In one embodiment, G is a phenyl group.

In one embodiment, G is a phenyl group substituted with one or more hydroxyl groups.

In one embodiment of the use or of the process, the compound is a compound of formula XV:

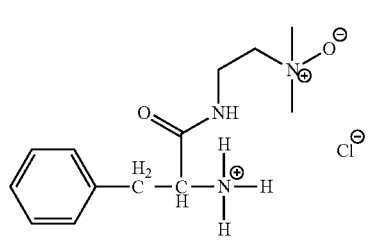

Formula XV in which:
the asymmetric carbon atoms have an R or S configuration.

In one embodiment of the use or of the process, the compound is chosen from the compounds of formula X:

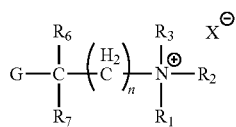

Formula X in which:
G is a C6 to C10 phenyl or alkylphenyl group, the phenyl group being substituted with one or more hydroxyl groups,
n is an integer equal to 1,
$R_1$, $R_2$ and $R_3$, which may be identical or different, are either a hydrogen atom or a chain comprising 1 to 4 carbon atoms, said chain possibly comprising one or more heteroatoms N or O,
$R_6$ is a chain comprising 1 to 6 carbon atoms, said chain possibly comprising one or more heteroatoms N or O, but does not bear any carboxylic acid functions,
$R_7$ is either a hydrogen atom or a chain comprising 1 to 6 carbon atoms, said chain possibly comprising one or more heteroatoms N or O, but does not bear any carboxylic acid functions,
$X^-$ is an anion chosen from the group consisting of halides, carboxylates, sulfates, phosphates and sulfonates,
the asymmetric carbon atoms have an R or S configuration.

In one embodiment, $R_6$ is either a hydrogen atom or a chain comprising 1 to 6 carbon atoms, said chain possibly comprising one or more functions chosen from the group consisting of hydroxyl, amide and ester functions.

In one embodiment, $R_6$ is a chain comprising 1 to 6 carbon atoms, said chain possibly comprising one or more functions chosen from the group consisting of hydroxyl, amide and ester functions.

In one embodiment, $R_6$ is not a hydrogen atom, and comprises an amine N-oxide function.

In one embodiment, $R_6$ is not a hydrogen atom, and comprises an amine N-oxide function and an amide function.

In one embodiment, $R_7$=H and $R_6$=

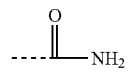

In one embodiment, $R_7$=H and $R_6$=—CH2OH
In one embodiment, $R_7$=H and $R_6$=

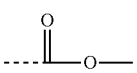

In one embodiment, $R_7$=H and $R_6$=

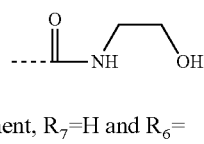

In one embodiment, $R_7$=H and $R_6$=

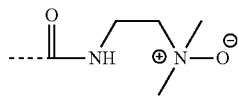

In one embodiment of the use or of the process, the compound is chosen from the compounds of formula XI:

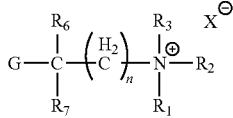

Formula XI in which:
G is a C6 to C10 phenyl or alkylphenyl group,
n is an integer equal to 1,
$R_1$, $R_2$ and $R_3$, which may be identical or different, are either a hydrogen atom or a chain comprising 1 to 4 carbon atoms, said chain possibly comprising one or more heteroatoms N or O,
$R_6$ is a chain comprising 1 to 6 carbon atoms, said chain possibly comprising one or more heteroatoms N or O, but does not bear any carboxylic acid functions,
$R_7$ is either a hydrogen atom or a chain comprising 1 to 6 carbon atoms, said chain possibly comprising one or more heteroatoms N or O, but does not bear any carboxylic acid functions,
$X^-$ is an anion chosen from the group consisting of halides, carboxylates, sulfates, phosphates and sulfonates,
the asymmetric carbon atoms are of R or S configuration.

In one embodiment, G is a phenyl group.

In one embodiment, $R_6$ is either a hydrogen atom or a chain comprising 1 to 6 carbon atoms, said chain possibly comprising one or more functions chosen from the group consisting of hydroxyl, amide and ester functions.

In one embodiment, $R_6$ is a chain comprising 1 to 6 carbon atoms, said chain possibly comprising one or more functions chosen from the group consisting of hydroxyl, amide and ester functions.

In one embodiment, $R_6$ is not a hydrogen atom, and comprises an amine N-oxide function.

In one embodiment, at least one group $R_6$ is not a hydrogen atom, and comprises an amine N-oxide function and an amide function.

In one embodiment, $R_7$=H and $R_6$=

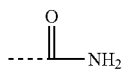

In one embodiment, $R_7$=H and $R_6$=—CH2OH
In one embodiment, $R_7$=H and $R_6$=

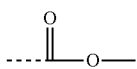

In one embodiment, $R_7$=H and $R_6$=

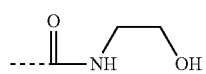

In one embodiment, $R_7$=H and $R_6$=

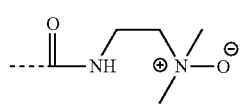

In one embodiment of the use or of the process, the compound is chosen from the compounds of formula VII:

Formula VII

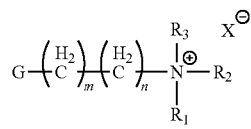

in which:
G is a C6 to C10 phenyl or alkylphenyl group, the phenyl group possibly being substituted with one or more hydroxyl groups,
m and n are integers, which may be identical or different, between 0 and 2 such that 0<m+n≤3,
$R_1$, $R_2$ and $R_3$, which may be identical or different, are either a hydrogen atom or a chain comprising 1 to 4 carbon atoms, said chain possibly comprising one or more heteroatoms N or O,
$X^-$ is an anion chosen from the group consisting of halides, carboxylates, sulfates, phosphates and sulfonates,
the asymmetric carbon atoms have an R or S configuration.
In one embodiment, G is a phenyl group.
In one embodiment, G is a phenyl group substituted with one or more hydroxyl groups.

In one embodiment of the use or of the process, m=n=1.
In one embodiment of the use or of the process, m=0 and n=1.
In one embodiment of the use or of the process, the compound is chosen from the compounds of formula VIII:

Formula VIII

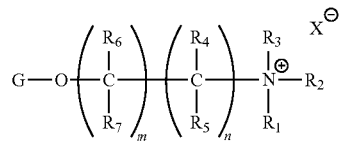

in which:
G is a C6 to C10 phenyl or alkylphenyl group, the phenyl group possibly being substituted with one or more hydroxyl groups,
m and n are integers, which may be identical or different, between 0 and 2 such that 0<m+n≤3,
$R_1$, $R_2$ and $R_3$, which may be identical or different, are either a hydrogen atom or a chain comprising 1 to 4 carbon atoms, said chain possibly comprising one or more heteroatoms N or O, but does not bear any carboxylic acid functions,
$R_4$ $R_5$, $R_6$ and $R_7$, which may be identical or different, are either a hydrogen atom or a chain comprising 1 to 6 carbon atoms, said chain possibly comprising one or more heteroatoms N or O, but does not bear any carboxylic acid functions,
$X^-$ is an anion chosen from the group consisting of halides, carboxylates, sulfates, phosphates and sulfonates,
the asymmetric carbon atoms have an R or S configuration.
In one embodiment, G is a phenyl group.
In one embodiment, G is a phenyl group substituted with one or more hydroxyl groups.
In one embodiment, $R_4$ and $R_6$, which may be identical or different, are either a hydrogen atom or a chain comprising 1 to 6 carbon atoms, said chain possibly comprising one or more functions chosen from the group consisting of hydroxyl, amide and ester functions.
In one embodiment, at least one group $R_4$, $R_5$, $R_6$ or $R_7$ is not a hydrogen atom, and comprises an amine N-oxide function.
In one embodiment, at least one group $R_4$, $R_5$, $R_6$ or $R_7$ is not a hydrogen atom, and comprises an amine N-oxide function and an amide function.
In one embodiment, $R_5$=$R_6$=$R_7$=H and $R_4$=

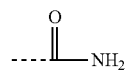

In one embodiment, $R_5$=$R_6$=$R_7$=H and $R_4$=—CH$_2$OH
In one embodiment, $R_5$=$R_6$=$R_7$=H and $R_4$=

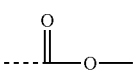

In one embodiment, $R_5$=$R_6$=$R_7$=H and $R_4$=

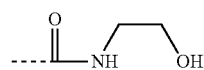

In one embodiment, $R_5=R_6=R_7=H$ and $R_4$

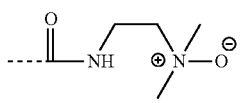

In one embodiment, $R_5=R_4=R_1=H$ and $R_6=$

In one embodiment, $R_5=R_4=R_7=H$ and $R_6=$—$CH_2OH$

In one embodiment, $R_5=R_4=R_7=H$ and $R_6=$

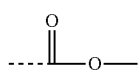

In one embodiment, $R_5=R_4=R_7=H$ and $R_6=$

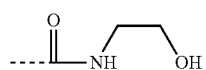

In one embodiment, $R_5=R_7=H$ and $R_6$

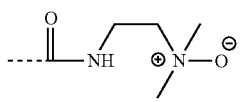

In one embodiment of the use or of the process, the compound of formula I is the phenylalaninamide hydrochloride salt and $R_1=R_2=R_3=H$, L is a bond, $G=C_6H_5$, $m=n=1$, $R_4=CONH_2$, $R_5=R_6=R_7=H$, and $X^-=Cl^-$ according to the formula:

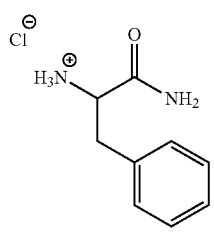

Formula XVI

In one embodiment of the use or of the process, the compound of formula I is the racemic mixture of the phenylalaninamide hydrochloride salt.

In one embodiment of the use or of the process, the compound of formula I is the L-phenylalaninamide hydrochloride salt.

In one embodiment of the use or of the process, the compound of formula I is the D-phenylalaninamide hydrochloride salt.

In one embodiment of the use or of the process, the compound of formula I is the 2-amino-3-phenyl-1-propanol hydrochloride salt and $R_1=R_2=R_3=H$, L is a bond, $G=C_6H_5$, $m=n=1$, $R_4=CH_2OH$, $R_5=R_6=R_7=H$, and $X^-=Cl^-$ according to the formula:

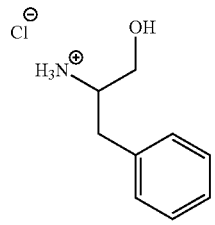

Formula XVII

In one embodiment of the use or of the process, the compound of formula I is the racemic mixture of the 2-amino-3-phenyl-1-propanol hydrochloride salt.

In one embodiment of the use or of the process, the compound of formula I is the (S)-(−)-2-amino-3-phenyl-1-propanol hydrochloride salt.

In one embodiment of the use or of the process, the compound of formula I is the (R)-(+)-2-amino-3-phenyl-1-propanol hydrochloride salt.

In one embodiment of the use or of the process, the compound of formula I is the phenylalanine methyl ester hydrochloride salt and $R_1=R_2=R_3=H$, L is a bond, $G=C_6H_5$, $m=n=1$, $R_4=COOCH_3$, $R_5=R_6=R_7=H$ and $X^-=Cl^-$ according to the formula:

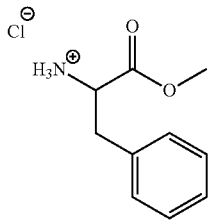

Formula XVIII

In one embodiment of the use or of the process, the compound of formula I is the racemic mixture of the phenylalanine methyl ester hydrochloride salt.

In one embodiment of the use or of the process, the compound of formula I is the L-phenylalanine methyl ester hydrochloride salt.

In one embodiment of the use or of the process, the compound of formula I is the D-phenylalanine methyl ester hydrochloride salt.

In one embodiment of the use or of the process, the compound of formula I is the α-amino-N-[2-(N-hydroxy-N,N-dimethylaminium)ethyl]benzenepropanamide dihydrochloride salt and $R_1=R_2=R_3=H$, L is a bond, $G=C_6H_5$, $m=n=1$, $R_4=CONHCH_2CH_2N(CH_3)_2O$, $R_5=R_6=R_7=H$ and $X^-=Cl^-$ of formula XV:

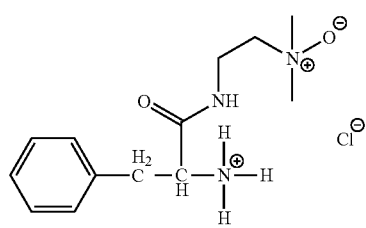

Formula XV

In one embodiment of the use or of the process, the compound of formula I is the racemic mixture of the α-amino-N-[2-(N-hydroxy-N,N-dimethylaminium)ethyl]benzenepropanamide dihydrochloride salt.

In one embodiment of the use or of the process, the compound of formula I is the D-α-amino-N-[2-(N-hydroxy-N,N-dimethylaminium)ethyl]benzene-propanamide dihydrochloride salt.

In one embodiment of the use or of the process, the compound of formula I is the L-α-amino-N-[2-(N-hydroxy-N,N-dimethylaminium)ethyl]benzene-propanamide dihydrochloride salt.

In one embodiment of the use or of the process, the compound of formula I is the 2-phenylethylamine hydrochloride salt and $R_1=R_2=R_3=H$, L is a bond, $G=C_6H_5$, $m=n=1$, $R_4=R_5=_7=H$ and $X^-=Cl^-$.

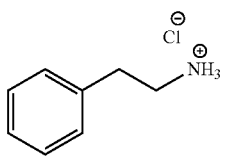

Formula XIX

In one embodiment of the use or of the process, the compound of formula I is benzyltriethylammonium chloride and $R_1=R_2=R_3=CH_3$, L is a bond, $G=C_6H_5$, $m=0$, $n=1$, $R_4=R_5=H$ and $X^-=Cl^-$.

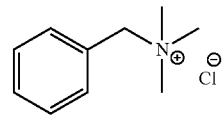

Formula XX

In one embodiment of the use or of the process, the compound of formula I is the salt (2S-2-amino(3-phenylpropanoyl)amino)ethanol hydrochloride and $R_1=R_2=R_3=H$, L is a bond, $G=C_6H_5$, $m=1$, $n=1$, $R_4=CONHCH_2CH_2OH$, $R_5=H$ and $X^-=Cl^-$.

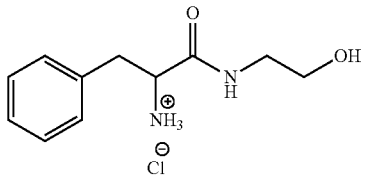

Formula XXI

In one embodiment of the use or of the process, the compound of formula I is the racemic mixture of the salt (2S-2-amino(3-phenylpropanoyl)amino)ethanol hydrochloride.

In one embodiment of the use or of the process, the compound of formula I is the salt (2S-2-amino(3-phenylpropanoyl)amino)ethanol hydrochloride.

In one embodiment of the use or of the process, the compound of formula I is the salt (2S-2-amino(3-phenylpropanoyl)amino)ethanol hydrochloride.

In one embodiment of the use or of the process, the compound of formula I is the dopamine hydrochloride salt and $R_1=R_2=R_3=CH_3$, L is a bond, $G=C_6H_5$, $m=1$, $n=1$, $R_4=R_5=R_6=R_7=H$ and $X^-=Cl^-$.

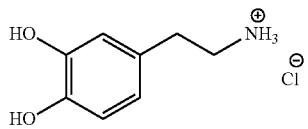

Formula XXII

In one embodiment of the use or of the process, the compound of formula I is the 2-phenoxyethylamine hydrochloride salt and $R_1=R_3=CH_3$, $L=O$, $G=C_6H_5$, $m=1$, $n=1$, $R_4=R_5=R_6=R_7=H$ and $X^-=Cl^-$.

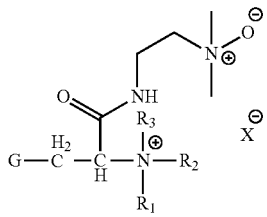

Formula XXIII

The present invention also relates to a viscosity-reducing compound of formula XIV:

Formula XIV in which:

G is a C6 to C10 phenyl or alkylphenyl group, the phenyl group possibly being substituted with one or more hydroxyl groups, $R_1$, $R_2$ and $R_3$, which may be identical or different, are either a hydrogen atom or a chain comprising 1 to 4 carbon atoms, said chain possibly comprising one or more heteroatoms N or O, $X^-$ is at least one anion chosen from the group consisting of halides, carboxylates, sulfates, phosphates and sulfonates, the asymmetric carbon atoms have an R or S configuration.

The present invention also relates to a viscosity-reducing compound of formula XV:

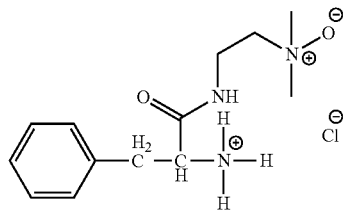

Formula XV in which:
the asymmetric carbon atoms have an R or S configuration.

The present invention also relates to an aqueous (reduced-viscosity) composition comprising a compound of formula XIV and a protein comprising at least one antibody fragment whose concentration is between 50 and 350 mg/mL and whose pH is between 5 and 8.

In one embodiment of the composition, the concentration of the compound of formula XIV is between 10 and 200 mM.

In one embodiment of the composition, the concentration of the compound of formula XIV is between 25 and 200 mM.

In one embodiment of the composition, the concentration of the compound of formula XIV is between 50 and 200 mM.

In one embodiment of the composition, the concentration of the compound of formula XIV is between 50 and 175 mM.

In one embodiment of the composition, the concentration of the compound of formula XIV is between 100 and 250 mM.

In one embodiment of the composition, the concentration of the compound of formula XIV is between 100 and 200 mM.

In one embodiment of the composition, the concentration of the compound of formula XIV is between 100 and 175 mM.

The present invention also relates to an aqueous (reduced-viscosity) composition comprising a compound of formula XV at a concentration of between 10 and 250 mM and a protein comprising at least one antibody fragment whose concentration is between 50 and 350 mg/mL and whose pH is between 5 and 8.

In one embodiment of the composition, the concentration of the compound of formula XV is between 10 and 200 mM.

In one embodiment of the composition, the concentration of the compound of formula XV is between 25 and 200 mM.

In one embodiment of the composition, the concentration of the compound of formula XV is between 50 and 200 mM.

In one embodiment of the composition, the concentration of the compound of formula XV is between 50 and 175 mM.

In one embodiment of the composition, the concentration of the compound of formula XV is between 100 and 250 mM.

In one embodiment of the composition, the concentration of the compound of formula XV is between 100 and 200 mM.

In one embodiment of the composition, the concentration of the compound of formula XV is between 100 and 175 mM.

In one embodiment of the composition, the concentration of protein comprising at least one antibody fragment is between 100 and 350 mg/mL.

In one embodiment of the composition, the concentration of protein comprising at least one antibody fragment is between 100 and 300 mg/mL.

In one embodiment of the composition, the concentration of protein comprising at least one antibody fragment is between 100 and 250 mg/mL.

In one embodiment of the composition, the concentration of protein comprising at least one antibody fragment is between 150 and 300 mg/mL.

In one embodiment of the composition, the concentration of protein comprising at least one antibody fragment is between 150 and 250 mg/mL.

The invention is illustrated by the examples that follow, which illustrate the technical effect and the comparison with the compounds of the prior art.

EXAMPLE 1

Preparation of Stock Solutions

In the table below, the compounds that are cited in the rest of the experimental section are described and identified by a code RV X or an abbreviated name Arg or a name NaCl.

| Code | Name | Structure | Supplier Reference | CAS number |
|---|---|---|---|---|
| Arg | L-arginine hydrochloride salt | 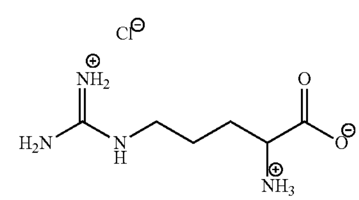 [SMILES: [Cl-] ; NC(=[NH2+])NCCCC([NH3+])C(=O)[O-]] | Sigma 11039 | CAS# 1119-34-2 |
| RV 1 | N/A | N/A | N/A | N/A |
| RV 2 | (2S-2-amino(3-phenylpropanoyl)amino)-ethanol hydrochloride salt | 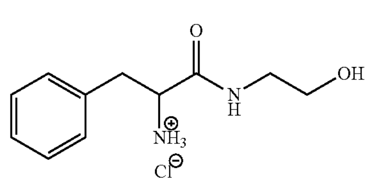 [SMILES: [NH3+]C(Cc1ccccc1)C(=O)NCCO ; [Cl-]] | Adocia | N/A |

-continued

| Code | Name | Structure | Supplier Reference | CAS number |
|---|---|---|---|---|
| RV 3 | L-phenylalanine methyl ester hydrochloride salt | 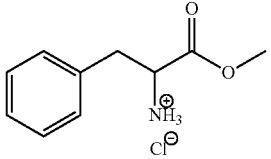 | Bachem E-2270 | CAS# 7524-50-7 |
| RV 4 | (S)-(−)-2-amino-3-phenyl-1-propanol hydrochloride salt | 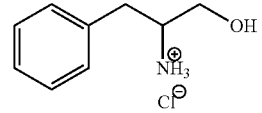 [SMILES: [NH3+]C(CO)Cc1ccccc1 ; [Cl-]] | Aldrich 190438 | CAS# 3182-95-4 |
| RV 5 | benzyltrimethylammonium chloride | 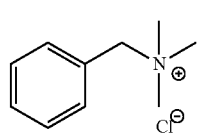 | Aldrich 228982 | CAS# 56-93-9 |
| RV 6 | 2-phenylethylamine hydrochloride salt | 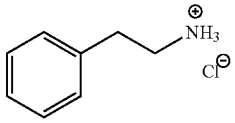 | Aldrich 241008 | CAS# 64-04-0 |
| RV 7 | dopamine hydrochloride salt | 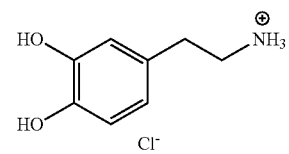 [SMILES: [NH3+]CCc1ccc(O)c(O)c1 ; [Cl-]] | Sigma H8502 | CAS# 62-31-7 |
| RV 8 | 2-phenoxyethylamine hydrochloride salt | 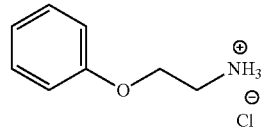 | Aldrich 448400 | CAS# 1758-46-9 |
| RV 9 | L-phenylalaninamide hydrochloride salt | 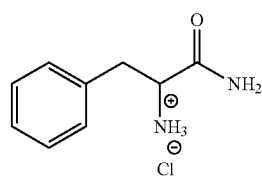 [SMILES: NC(=O)C(N)Cc1ccccc1 ; Cl] | Bachem E-2235 | CAS# 5241-58-7 |
| RV 9a | L-phenylalaninamide acetate salt | 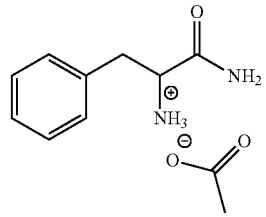 | Adocia | N/A |
| RV 9b | L-phenylalaninamide sulfate salt | 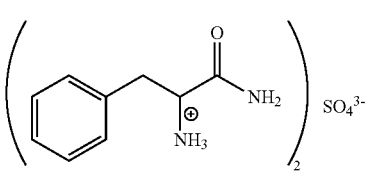 | Adocia | N/A |

-continued

| Code | Name | Structure | Supplier Reference | CAS number |
|---|---|---|---|---|
| RV 9c | L-phenylalaninamide phosphate salt | (structure shown) | Adocia | N/A |
| NaCl | sodium chloride | Na⁺Cl⁻ | Cooper 171 0500 | CAS# 7647-14-5 |
| RV 10 | N/A | N/A | N/A | N/A |
| RV 11 | α-amino-N-[2-(N,N-dimethylamine-N-oxido)ethyl]benzene-propanamide hydrochloride salt | (structure shown) | Adocia | N/A |

N/A means not applicable.

Arg: Solution of L-Arginine Hydrochloride Salt

The salt L-arginine hydrochloride was obtained from Sigma-Aldrich (Sigma Ref. 11039, CAS#1119-34-2) and was dissolved in Milli-Q® water so as to obtain a 994 mM solution of L-arginine hydrochloride salt.

RV 2: Solution of (2S-2-Amino(3-Phenylpropanoyl)Amino) Ethanol Hydrochloride Salt 10 g (37.7 mmol) of N-tert-butoxycarbonyl-L-phenylalanine are added to 2.4 g (40 mmol) of ethanolamine dissolved in dichloromethane. The mixture is cooled to 0° C. and 11.2 g (87 mmol) of diisopropylamine and 5.1 g (37.7 mmol) of hydroxybenzotriazole hydrate are then added. 9.4 g (49 mmol) of N-(3-dimethylaminopropyl)-N'-ethylcarbodiimide hydrochloride are then added and the mixture is stirred at room temperature for 70 hours. The reaction medium is washed with half-saturated $NH_4Cl$ solution, saturated $NaHCO_3$ solution and water, and after drying over $MgSO_4$, the organic phase is concentrated to give 11.6 g of ((2S-2-[(tert-butoxycarbonyl)amino]-3-phenylpropanoyl)amino) ethanol.

85 ml of a solution (4M) of HCl in dioxane are gradually added to 10.5 g (34 mmol) of ((2S-2-[(tert-butoxycarbonyl) amino]-3-phenylpropanoyl)amino)ethanol in dichloromethane at 0° C. After leaving overnight at room temperature, the reaction medium is concentrated and the solid obtained is washed with diisopropylether and then dried under vacuum. 7.3 g of (2S-2-amino(3-phenylpropanoyl) amino)ethanol hydrochloride salt are obtained.

The product is recrystallized from ethanol to give a white solid.

Yield: 3.8 g (43%)

$^1$H NMR (DMSO-$d_6$, ppm): 3.00-3.20 (4H); 3.25-3.40 (2H); 3.99 (1H); 4.81 (1H); 7.25-7.35 (5H); 8.38 (3H); 8.66 (1H).

LC/MS (ESI): 207.1 ([M−Cl−H]⁻); ([M−Cl−H]⁻ calculated: 208.2).

This salt was then dissolved in Milli-Q® water so as to obtain a 1019 mM solution of (2S-2-amino(3-phenylpropanoyl)amino)ethanol hydrochloride salt.

RV 3: Solution of L-Phenylalanine Methyl Ester Hydrochloride Salt

The L-phenylalanine methyl ester hydrochloride salt (RV 3) was obtained from Bachem (Ref E-2270, CAS#7524-50-7) and was dissolved in Milli-Q® water so as to obtain a 998 mM solution of L-phenylalanine methyl ester hydrochloride salt.

RV 4: Solution of (S)-(−)-2-Amino-3-Phenyl-1-Propanol Hydrochloride Salt

The salt (S)-(−)-2-amino-3-phenyl-1-propanol hydrochloride (RV 4) was obtained by dissolving (S)-(−)-2-amino-3-phenyl-1-propanol, obtained from Sigma-Aldrich (Aldrich ref. 190438, CAS#3182-95-4) in Milli-Q® water and by adding hydrochloric acid (HCl) so as to obtain a 992 mM solution of the (S)-(−)-2-amino-3-phenyl-1-propanol hydrochloride salt.

RV 5: Benzyltrimethylammonium Chloride

Benzyltrimethylammonium chloride (RV 5) was obtained from Sigma-Aldrich (Aldrich ref. 228982, CAS#56-93-9) and was dissolved in Milli-Q® water so as to obtain a 1030 mM solution of benzyltrimethylammonium chloride.

RV 6: Solution of 2-Phenylethylamine Hydrochloride Salt

The 2-phenylethylamine hydrochloride salt (RV 6) was obtained by dissolving 2-phenylethylamine obtained from Sigma-Aldrich (Sigma ref. 241008, CAS#64-04-0) in Milli-Q® water and by adding hydrochloric acid so as to obtain an 881 mM solution of 2-phenylethylamine hydrochloride salt.

RV 7: Solution of Dopamine Hydrochloride Salt

The dopamine hydrochloride salt (RV 7) was obtained from Sigma-Aldrich (Sigma ref. H8502, CAS#62-31-7) and was dissolved in Milli-Q® water so as to obtain a 1071 mM solution of dopamine hydrochloride salt.

RV8: Solution of 2-Phenoxyethylamine Hydrochloride Salt

The 2-phenoxyethylamine hydrochloride salt (RV 8) was obtained by dissolving 2-phenoxyethylamine obtained from Sigma-Aldrich (Aldrich ref. 448400, CAS#1758-46-9) in hydrochloric acid so as to obtain an 826 mM solution of 2-phenoxyethylamine hydrochloride salt.

RV 9: Solution of L-Phenylalaninamide Hydrochloride Salt

The L-phenylalaninamide hydrochloride salt (RV 9) was obtained by dissolving L-phenylalaninamide, obtained from Bachem (Ref E-2235, CAS#5241-58-7) in Milli-Q® water and by adding hydrochloric acid so as to obtain a 955 mM solution of the salt L-phenylalaninamide hydrochloride.

RV 9a: Solution of L-Phenylalaninamide Acetate Salt

The L-phenylalaninamide acetate salt (RV 9a) was obtained by dissolving L-phenylalaninamide, obtained from Bachem (Ref E-2235, CAS#5241-58-7), in Milli-Q® water and by adding acetic acid so as to obtain an 1196 mM solution of L-phenylalaninamide acetate salt.

RV 9b: Solution of L-Phenylalaninamide Sulfate Salt

The L-phenylalaninamide sulfate salt (RV 9b) was obtained by dissolving L-phenylalaninamide, obtained from Bachem (Ref E-2235, CAS#5241-58-7), in Milli-Q® water and by adding sulfuric acid so as to obtain a 1250 mM solution of L-phenylalaninamide sulfate salt.

RV 9c: Solution of L-Phenylalaninamide Phosphate Salt

The L-phenylalaninamide phosphate salt (RV 9c) was obtained by dissolving L-phenylalaninamide, obtained from Bachem (Ref E-2235, CAS#5241-58-7), in Milli-Q® water and by adding phosphoric acid so as to obtain a 1250 mM solution of L-phenylalaninamide phosphate salt.

RV 11: Solution of α-Amino-N-[2-(N,N-Dimethylamine-N-Oxido)Ethyl]Benzenepropanamide Hydrochloride Salt 10 g (113 mmol) of N,N'-dimethylethylene-1,2-diamine and 15.25 g (150.8 mmol) of N-methylmorpholine are added, at room temperature, to a solution of 21.7 g (113 mmol) of N-(3-dimethylaminopropyl)-N'-ethylcarbodiimide hydrochloride, 17.3 g (113 mmol) of 1-hydroxybenzotriazole and 20 g (75.4 mmol) of N-tert-butoxycarbonyl-L-phenylalanine in DMF. The mixture is stirred at room temperature for 24 hours, concentrated under reduced pressure and extracted with ethyl acetate. The organic phase is washed with saturated $NaHCO_3$ solution and then dried over $Na_2SO_4$, filtered and concentrated under reduced pressure to give a yellow solid. By recrystallization using ethyl acetate, [(1S)-2-[(2-dimethylamino)ethyl]amino]-2-oxo-1-(phenylmethyl)ethyl]carbamate is obtained in the form of a white solid.

Yield: 12.9 g (51%).

$^1$H NMR (DMSO-$d_6$, ppm): 1.2-1.3 (9H); 2.12 (6H), 2.21-2.25 (2H), 2.68-2.72 (1H), 2.85-2.90 (1H), 3.05-3.20 (2H), 4.05-4.15 (1H), 6.89-6.92 (1H), 7.10-7.25 (5H), 7.73 (1H).

LC/MS (ESI): 336.6 ([M+H]$^+$); ([M+H]$^+$ calculated: 335.5).

A solution of meta-chloroperbenzoic acid (13.5 g) in chloroform (88 mL) is added, under an inert atmosphere and at 0° C., to a solution of 12.9 g (38.45 mmol) of [(1S)-2-[(2-dimethylamino)ethyl]amino]-2-oxo-1-(phenylmethyl)ethyl]carbamate in chloroform (77 mL). After reaction for 10 minutes, the medium is poured into saturated $Na_2CO_3$ solution and the aqueous phase is extracted three times with chloroform. The combined organic phases are washed with saturated NaCl solution and then dried over $Na_2SO_4$. The pH of the aqueous phase is raised to 12, and the resulting mixture is extracted three times with ethyl acetate. The organic phases are combined, dried over $Na_2SO_4$ and, after concentration, a white solid is obtained. This solid is used without further purification in the following step of deprotection of the primary amine function. 54 mL of HCl (4N) in dioxane are added, under an inert atmosphere and at 0° C., to a solution of the white solid (10.8 g) in dichloromethane (150 mL). After stirring for 3 hours at 0° C., the medium is extracted with 3×100 mL of an HCl solution (1N). The combined aqueous phases are washed with 60 mL of dichloromethane, filtered and concentrated under reduced pressure. The yellow oil obtained is taken up in 50 mL of absolute ethanol and the precipitated NaCl is removed by filtration on a sinter funnel. The white solid obtained after concentrating under reduced pressure is purified by recrystallization from ethanol to give white crystals. The product is taken up in 30 mL of water and lyophilized.

Yield: 5.7 g (57%).

$^1$H NMR (DMSO-$d_6$, ppm): 3.05-3.10 (2H), 3.35-3.75 (10H), 4.05 (1H), 7.25-7.35 (5H), 8.52 (3H) 9.19-9.22 (1H), 12.87 (1H).

LC/MS (ESI): 252.6 ([M−2Cl−H])$^-$; ([M−2Cl−H]$^-$ calculated: 253.2).

The lyophilizate of the salt α-amino-N-[2-(N-hydroxy-N,N-dimethylaminium)ethyl]benzenepropanamide dihydrochloride thus obtained is dissolved in Milli-Q® water with addition of sodium hydroxide so as to obtain a 1223 mM solution of α-amino-N-[2-(N-hydroxy-N,N-dimethylaminium)ethyl]benzenepropanamide dihydrochloride.

EXAMPLE 2

Effect of RVs 2 and 9 Comparatively with that of Arg and NaCl on the Viscosity of Various Highly Concentrated Therapeutic Protein Solutions This example illustrates how two of the RVs belonging to the family of RVs used according to the invention, RV 2 and RV 9, reduce the viscosity of three formulations of monoclonal antibodies and of a formulation of fusion protein in comparison with reference compounds such as Arg and NaCl.

For this example, three solutions of monoclonal antibodies, i.e. a solution of bevacizumab (an IgG1 sold under the name Avastin® by Genentech/Hoffmann La Roche), a solution of infliximab (an IgG1/K sold under the name Remicade® by Schering-Plough), a solution of rituximab (an IgG1/K sold under the name mAbThera® by Hoffmann La Roche) and a solution of fusion protein, i.e. a solution of abatacept (IgG1-CTLA4 sold under the name Orencia® by Bristol-Meyers Squibb), were concentrated by ultrafiltration on Amicon® Ultra-15 filtration units with a cutoff threshold of 50 kDa.

The protein concentration of each concentrated solution was measured by UV spectroscopy (absorbance at 280 nm) after gravimetric dilution of the samples.

The solutions of rituximab (10 mg/mL) and of bevacizumab (25 mg/mL) were concentrated, respectively, to 320 mg/mL and 240 mg/mL.

Infliximab and abatacept, sold in the form of lyophilizate, were reconstituted with water for injection to the concentration suggested by the manufacturer (i.e. 10 mg/mL for infliximab and 25 mg/mL for abatacept) and then concentrated, respectively, to 199 mg/mL and 280 mg/mL.

The pH values of the commercial formulations of therapeutic proteins used for these tests are collated in the table below:

|  | rituximab | bevacizumab | infliximab | abatacept |
|---|---|---|---|---|
| pH of the commercial formulation | 6.5 ± 0.2 | 6.2 ± 0.2 | 7.2 ± 0.2 | 7.5 ± 0.5 |

The effect of RVs 2 and 9 on the viscosity of these four highly concentrated therapeutic protein solutions was then evaluated comparatively with that of Arg and NaCl. To do this, the viscosity was measured using a cone/plate rheometer (TA Instrument, AR 2000 Ex, geometry of diameter 20 mm, cone of 0.5131°, solvent trap filled with water) at a temperature of 21° C. and in flow sweep mode with shear rates of between 5000 and 50 s$^{-1}$ (3 points per decade—steady-state sensing).

For this example, the "protein+RV", "protein+Arg" and "protein+NaCl" formulations were prepared by mixing one of the solutions of RV, Arg or NaCl prepared in example 1 and one of the concentrated protein solutions prepared previously so as to reach a final concentration of RV, Arg or NaCl of 150 mM and a final protein concentration of 250 mg/mL for bevacizumab, 196 mg/mL for rituximab, 230 mg/mL for abatacept and 107 mg/mL for infliximab. The samples thus prepared were stored at room temperature and were analyzed using the rheometer within 24 hours of their preparation.

The control solutions are prepared by dilution in Milli-Q® water, so as to reach a final protein concentration of 250 mg/mL for bevacizumab, 196 mg/mL for rituximab, 230 mg/mL for abatacept and 107 mg/mL for infliximab. The pH of these formulations is the same as that of the commercial formulation of the corresponding therapeutic protein.

The results of the measurements relating to this second example are presented in table I below in the form of percentages of viscosity reduction relative to the control solution of therapeutic protein alone, at the same protein concentration as the "protein+RV" or "protein+Arg" or "protein+NaCl" formulations.

TABLE I

| Concentration Tested | % viscosity reduction relative to the control "protein alone" | | | |
|---|---|---|---|---|
| | bevacizumab 250 mg/mL | rituximab 196 mg/mL | abatacept 230 mg/mL | infliximab 107 mg/mL |
| 150 mM NaCl | ≤0% | 21% | 7% | ≤0% |
| 150 mM Arg | 26% | 58% | 31% | 32% |
| 150 mM RV 2 | 44% | 43% | 27% | 56% |
| 150 mM RV 9 | 35% | 48% | 42% | 52% |

The data presented in table I show that in the presence of 150 mM of RV 2 or of RV 9, the viscosity of the 4 highly concentrated protein solutions is significantly reduced.

EXAMPLE 3

Effect of Various RVs on the Viscosity of Two Aqueous Formulations of Highly Concentrated Monoclonal Antibodies Comparatively with that of Arg and NaCl This example illustrates how different RVs used according to the invention lower the viscosity of highly concentrated solutions of infliximab and of rituximab in comparison with a reference such as Arg and NaCl.

In this study, the highly concentrated infliximab and rituximab solutions used are the same as those which were prepared and used previously. The "protein+RV" formulations were prepared in the presence of 150 mM of different RVs used according to the invention. The viscosity of these formulations was then measured as described in example 2 and compared with that obtained in the presence of Arg at 150 mM. The pH of these formulations is the same as that of the corresponding therapeutic protein formulation, i.e. 7.2±0.2 for infliximab, and 6.5±0.2 for rituximab.

The results of the measurements relating to this third example are presented in tables II and III below in the form of percentages of viscosity reduction relative to the control solution of therapeutic protein alone, at the same protein concentration as the "protein+RV" or "protein+Arg" or "protein+NaCl" formulations.

TABLE II

| | Concentration Tested | % viscosity reduction relative to the control "protein alone" |
|---|---|---|
| infliximab 107 mg/mL | 150 mM NaCl | ≤0% |
| | 150 mM Arg | 32% |
| | 150 mM RV 4 | 36% |
| | 150 mM RV 6 | 38% |
| | 150 mM RV 7 | 38% |
| | 150 mM RV 8 | 46% |
| | 150 mM RV 5 | 49% |
| | 150 mM RV 9 | 52% |
| | 150 mM RV 2 | 56% |
| | 150 mM RV 3 | 64% |

The data presented in table II demonstrate that, when used at 150 mM, all the RVs used according to the invention reduce the viscosity of infliximab at 107 mg/mL significantly.

TABLE III

| | Concentration tested | % viscosity reduction relative to the control "protein alone" |
|---|---|---|
| rituximab 196 mg/mL | 150 mM NaCl | 21% |
| | 150 mM Arg | 58% |
| | 150 mM RV 3 | 28% |
| | 150 mM RV 4 | 37% |
| | 150 mM RV 5 | 38% |
| | 150 mM RV 6 | 39% |
| | 150 mM RV 7 | 39% |
| | 150 mM RV 2 | 43% |
| | 150 mM RV 9 | 48% |
| | 150 mM RV 8 | 52% |

The data presented in table III demonstrate that, when used at 150 mM, all the RVs used according to the invention reduce the viscosity of rituximab at 196 mg/mL significantly.

EXAMPLE 4

Evaluation of the Effect of the Concentration of RV 9 on the Reduction in Viscosity of an Aqueous Formulation of Highly Concentrated Monoclonal Antibody Comparatively with that of Arg The highly concentrated infliximab solution used is the same as that which was prepared and used previously. The "protein+RV" formulations were prepared in the presence of concentrations increasing from 0 to 200 mM of Arg or RV 9. The pH of these formulations is the same as that of the commercial infliximab formulation, i.e. 7.2±0.2.

The viscosity of the formulations thus prepared was measured as described in example 2.

The results of the measurements relating to this fourth example are presented in table IV below in the form of percentages of viscosity reduction relative to the control solution of therapeutic protein alone, at the same protein concentration as the "protein+RV" formulations.

TABLE IV

| | Concentration tested | Arg % viscosity reduction relative to the control "protein alone" | RV 9 % viscosity reduction relative to the control "protein alone" |
|---|---|---|---|
| infliximab 107 mg/mL | 25 mM | 9% | 19% |
| | 50 mM | 13% | 31% |
| | 100 mM | 9% | 41% |
| | 150 mM | 31% | 44% |
| | 200 mM | 34% | 56% |

The data presented in table IV show that at 150 mM, RV 9 is already twice as efficient as Arg. At 100 mM, RV 9 is about 4 times as efficient as Arg. Moreover, these results also show that 50 mM of RV 9 are sufficient to obtain a viscosity reduction equivalent to that obtained using Arg at 150 mM.

EXAMPLE 5

Evaluation of the Effect of the Concentration of a Monoclonal Antibody on the Lowering of Viscosity in the Presence of the RVs Used According to the Invention The object of this example is to compare the efficacy in viscosity reduction of RV 9 with that of Arg, as a function of the antibody concentration.

The highly concentrated infliximab solution used is the same as that which was prepared and used previously. The "protein+RV" formulations were prepared in the presence of 150 mM of Arg or RV 9 and of concentrations increasing from 80 mg/mL to 110 mg/mL of infliximab.

The pH of these formulations is the same as that of the commercial infliximab formulation, i.e. 7.2±0.2.

The viscosity of the formulations thus prepared was measured as described in example 2.

The results of the measurements relating to this fifth example are presented in table V below in the form of percentages of viscosity reduction relative to the control infliximab solution.

TABLE V

| infliximab concentration | % viscosity reduction relative to the control infliximab solution | |
|---|---|---|
| (mg/mL) | Arg at 150 mM | RV 9 at 150 mM |
| 80 | 25% | 50% |
| 90 | 30% | 52% |
| 100 | 39% | 55% |
| 110 | 22% | 49% |

The data presented in table V show that irrespective of the infliximab concentration, Arg lowers the viscosity of the solution by only about 29% on average, whereas RV 9 lowers it by about 52% on average.

EXAMPLE 6

Evaluation of the Effect of the Counterion of an RV Used According to the Invention on the Viscosity Lowering of an Aqueous Formulation of Highly Concentrated Monoclonal Antibody Afforded by this RV The object of this example is to evaluate the impact of the counterion (in the present case the counter-anion) on the viscosity lowering of an infliximab solution at 115 mg/mL in the presence of modified RV 9, where HCl has been replaced with various counterions. The counter-anions tested are: chloride (RV 9), acetate (RV 9a), phosphate (RV 9b) and sulfate (RV 9c).

The highly concentrated infliximab solution used was prepared in the same manner as that used previously. The "protein+RV" formulations were prepared by addition of a solution of RV (9, 9a, 9b or 9c) prepared in example 2 (at about 1.2 M) and Milli-Q® water to the concentrated infliximab solution so as to reach a final RV concentration of 150 mM and a final protein concentration of 115 mg/mL. The pH of these formulations is the same as that of the commercial infliximab formulation, i.e. 7.2±0.2. The viscosity of the formulations thus prepared was measured as described in example 2. The results of the measurements relating to this sixth example are presented in table VI below in the form of percentages of viscosity reduction relative to the control solution of therapeutic protein alone, at the same protein concentration.

TABLE VI

| | Concentration tested | % viscosity reduction relative to the control "protein alone" |
|---|---|---|
| infliximab 115 mg/mL | 150 mM RV 9 | 64% |
| | 150 mM RV 9a | 54% |
| | 150 mM RV 9b | 54% |
| | 150 mM RV 9c | 56% |

The data presented in table VI show that RV 9, RV 9a, RV 9b and RV 9c all reduce the viscosity of infliximab at 115 mg/mL by at least 54%.

EXAMPLE 7

Effect of RVs 2 and 11 on the Viscosity of Various Highly Concentrated Therapeutic Protein Formulations Comparatively with that of Arg and NaCl This example illustrates how RV 2 and RV 11 belonging to the family of RVs used according to the invention reduce the viscosity of two monoclonal antibody formulations in comparison with reference compounds such as Arg and NaCl.

For this example, two monoclonal antibody formulations, i.e. infliximab and trastuzumab (an IgG1/κ sold under the name Herceptin® by Genentech) were concentrated by ultrafiltration on Amicon® Ultra-50 centrifugal filtration units with a cutoff threshold of 50 kDa. The protein concentration of each concentrated solution was measured by UV spectroscopy (absorbance at 280 nm) after gravimetric dilution of the samples.

The monoclonal antibodies infliximab and trastuzumab, sold in the form of lyophilizates, were reconstituted with water for injection at the concentration suggested by the manufacturers (i.e. 10 mg/mL for infliximab and 21 mg/mL for trastuzumab). Once reconstituted, the infliximab and trastuzumab formulations were concentrated, respectively, to 212 mg/mL and 277 mg/mL.

The pH of the commercial formulations of therapeutic proteins used for these tests is indicated in the table below:

| | infliximab | trastuzumab |
|---|---|---|
| pH of the commercial formulation | 7.2 ± 0.2 | 6 ± 0.2 |

The effect of RVs 2 and 11 on the viscosity of these two highly concentrated therapeutic protein formulations was then evaluated comparatively to that of Arg and NaCl. To do this, the viscosity was measured using a cone/plate rheometer (TA Instrument, AR 2000 Ex, geometry of diameter 20 mm, cone of 0.5131°, solvent trap filled with water) at a temperature of 25° C. and in flow sweep mode with shear rates of between 5000 and 50 s$^{-1}$ (3 points per decade—steady-state sensing).

For this example, the "protein+RV" formulations were prepared by mixing a solution of RV at about 1 M obtained in example 1 with one of the concentrated infliximab and trastuzumab formulations prepared previously and the corresponding buffer so as to reach a final RV concentration of 150 mM and a final protein concentration of 125 mg/mL for infliximab and 200 mg/mL for trastuzumab. The samples thus prepared were stored at room temperature and were analyzed using a rheometer within 72 hours of their preparation.

The control solutions are prepared by dilution in Milli-Q® water, so as to reach a final protein concentration of 125 mg/mL for infliximab and 200 mg/mL for trastuzumab. The pH of these formulations is the same as that of the corresponding commercial formulation of therapeutic protein.

The results of the measurements relating to this second example are presented in table VII below in the form of percentages of viscosity reduction relative to the control solution of therapeutic protein alone, at the same protein concentration as the "protein+RV" formulations.

TABLE VII

| Concentration tested | % of viscosity reduction relative to the control "protein alone" | |
|---|---|---|
| | infliximab 125 mg/mL | trastuzumab 200 mg/mL |
| 150 mM NaCl | ≤0% | 38% |
| 150 mM Arg | 11% | 56% |
| 150 mM RV 2 | 44% | 63% |
| 150 mM RV 11 | 42% | 52% |

The data presented in table VII demonstrate that in the presence of 150 mM of RV 2 or 11, the viscosity of the two highly concentrated protein solutions is significantly reduced.

EXAMPLE 8

Examples of Compositions According to the Invention 8.1 Composition in the Form of a Highly Concentrated Infliximab Solution Whose pH is 7.2, Comprising RV 11.

| Composition 1 | |
|---|---|
| Ingredient: | Concentration: |
| Infliximab | 125 mg/mL |
| Sodium phosphate | 30 mM |
| Sucrose | 86 mM |
| Polysorbate 80 | 474 μM |
| α-amino-N-[2-(N,N-dimethylamine-N-oxide)ethyl] benzenepropanamide hydrochloride salt (RV 11) | 150 mM |
| Water for injection, USP | qs |

8.2 Composition in the Form of a Highly Concentrated Trastuzumab Solution Whose pH is 6.0, Comprising RV 11

| Composition 2 | |
|---|---|
| Ingredient: | Concentration: |
| Trastuzumab | 200 mg/mL |
| L-Histidine | 1.7 mM |
| α,α-trehalose dehydrate | 38 mM |
| Polysorbate 20 | 653 μM |
| α-amino-N-[2-(N,N-dimethylamine-N-oxide)ethyl] benzenepropanamide hydrochloride salt (RV 11) | 150 mM |
| Water for injection, USP | qs |

8.3 Composition in the Form of a Highly Concentrated Trastuzumab Solution Whose pH is 6.0, Comprising RV 2

| Composition 3 | |
|---|---|
| Ingredient: | Concentration: |
| Trastuzumab | 200 mg/mL |
| L-Histidine | 1.7 mM |
| α,α-trehalose dehydrate | 38 mM |
| Polysorbate 20 | 675 μM |
| (2S-2-amino(3-phenyl-propanoyl)amino)ethanol hydrochloride salt (RV 2) | 150 mM |
| Water for injection, USP | qs |

8.4 Composition in the Form of a Highly Concentrated Infliximab Solution Whose pH is 7.2, Comprising RV 3

| Composition 4 | |
|---|---|
| Ingredient: | Concentration: |
| Infliximab | 107 mg/mL |
| Sodium phosphate | 27 mM |
| Sucrose | 79 mM |
| Polysorbate 80 | 411 μM |
| L-phenylalanine methyl ester hydrochloride salt (RV 3) | 150 mM |
| Water for injection, USP | qs |

8.5 Composition in the Form of a Highly Concentrated Rituximab Solution Whose pH is 6.5, Comprising RV 4

| Composition 5 | |
|---|---|
| Ingredient: | Concentration: |
| Rituximab | 196 mg/mL |
| Sodium citrate dihydrate | 15.33 mM |
| Sodium Chloride | 94 mM |
| Polysorbate 80 | 10.5 mM |
| (S)-(−)-2-amino-3-phenyl-1-propanol hydrochloride salt (RV 4) | 150 mM |
| Water for injection, USP | qs |

8.6 Composition in the Form of a Highly Concentrated Infliximab Solution Whose pH is 7.2, Comprising RV 5

| Composition 6 | |
|---|---|
| Ingredient: | Concentration: |
| Infliximab | 107 mg/mL |
| Sodium phosphate | 27 mM |
| Sucrose | 79 mM |
| Polysorbate 80 | 411 μM |
| Benzyltrimethylammonium chloride (RV 5) | 150 mM |
| Water for injection, USP | qs |

8.7 Composition in the Form of a Highly Concentrated Rituximab Solution Whose pH is 6.5, Comprising RV 6

| Composition 7 | |
|---|---|
| Ingredient: | Concentration: |
| Rituximab | 196 mg/mL |
| Sodium citrate dihydrate | 15.33 mM |
| Sodium Chloride | 94 mM |
| Polysorbate 80 | 10.5 mM |
| 2-phenylethylamine hydrochloride salt (RV 6) | 150 mM |
| Water for injection, USP | qs |

8.8 Composition in the Form of a Highly Concentrated Rituximab Solution Whose pH is 6.5, Comprising RV 7

| Composition 8 | |
|---|---|
| Ingredient: | Concentration: |
| Rituximab | 196 mg/mL |
| Sodium citrate dihydrate | 15.33 mM |
| Sodium Chloride | 94 mM |
| Polysorbate 80 | 10.5 mM |
| Dopamine hydrochloride salt (RV 7) | 150 mM |
| Water for injection, USP | qs |

8.9 Composition in the Form of a Highly Concentrated Rituximab Solution Whose pH is 6.5, Comprising RV 8

| Composition 9 | |
|---|---|
| Ingredient: | Concentration: |
| Rituximab | 196 mg/mL |
| Sodium citrate dihydrate | 15.33 mM |
| Sodium Chloride | 94 mM |
| Polysorbate 80 | 10.5 mM |
| 2-Phenoxyethylamine hydrochloride salt (RV 8) | 150 mM |
| Water for injection, USP | qs |

8.10 Composition in the Form of a Highly Concentrated Infliximab Solution Whose pH is 7.2, Comprising RV 9

| Composition 10 | |
|---|---|
| Ingredient: | Concentration: |
| Infliximab | 115 mg/mL |
| Sodium phosphate | 29 mM |
| Sucrose | 85 mM |
| Polysorbate 80 | 440 μM |
| L-phenylalaninamide hydrochloride salt (RV 9) | 150 mM |
| Water for injection, USP | qs |

8.11 Composition in the Form of a Highly Concentrated Infliximab Solution Whose pH is 7.2, Comprising RV 9a

| Composition 11 | |
|---|---|
| Ingredient: | Concentration: |
| Infliximab | 115 mg/mL |
| Sodium phosphate | 29 mM |
| Sucrose | 85 mM |
| Polysorbate 80 | 440 μM |
| L-phenylalaninamide acetate salt (RV 9a) | 150 mM |
| Water for injection, USP | qs |

8.12 Composition in the Form of a Highly Concentrated Infliximab Solution Whose pH is 7.2, Comprising RV 9b

| Composition 12 | |
|---|---|
| Ingredient: | Concentration: |
| Infliximab | 115 mg/mL |
| Sodium phosphate | 29 mM |
| Sucrose | 85 mM |
| Polysorbate 80 | 440 μM |
| L-phenylalaninamide sulfate salt (RV 9b) | 150 mM |
| Water for injection, USP | qs |

8.13 Composition in the Form of a Highly Concentrated Infliximab Solution Whose pH is 7.2, Comprising RV 9c

| Composition 13 | |
|---|---|
| Ingredient: | Concentration: |
| Infliximab | 115 mg/mL |
| Sodium phosphate | 29 mM |
| Sucrose | 85 mM |
| Polysorbate 80 | 440 μM |
| L-phenylalaninamide phosphate salt (RV 9c) | 150 mM |
| Water for injection, USP | qs |

The invention claimed is:

1. A process of lowering the viscosity of an initial solution of at least one protein comprising at least one antibody fragment whose concentration is between 50 and 350 mg/mL and whose pH is between 5 and 8, comprising introducing to the initial solution a compound of formula I at a concentration in the final formulation of between 10 and 250 mM:

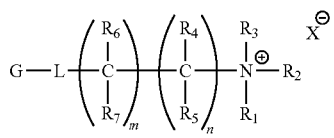

Formula I in which:

G is a C6 to C10 phenyl or alkylphenyl group, the phenyl group optionally being substituted with one or more hydroxyl groups, L is either a bond or a function chosen from the group consisting of the ether function, the carbamate function and the amide function, m and n are identical or different integers between 0 and 2 such that $0<m+n\leq 3$, $R_1$, $R_2$ and $R_3$, which may be identical or different, are either a hydrogen atom or a chain comprising 1 to 4 carbon atoms, said chain optionally comprising one or more N or O heteroatoms, $R_4$, $R_5$, $R_6$ and $R_7$, which may be identical or different, are either a hydrogen atom or a chain comprising 1 to 6 carbon atoms, but does not bear any carboxylic acid functions, $X^-$ is an anion chosen from the group consisting of halides, carboxylates, sulfates, phosphates and sulfonates, the asymmetric carbon atoms have an R or S configuration, the compound having a solubility in water of $\geq 20$ mM at a pH of between 5 and 8, wherein the process lowers the viscosity of the initial solution by a value of at least 15% relative to the viscosity of a solution of at least one protein comprising at least one antibody fragment of the same concentration and of the same pH not containing the compound.

2. The process as claimed in claim 1, wherein the viscosity reduction is between 20% and 95% relative to the viscosity of the initial solution.

3. The process as claimed in claim 1, wherein the viscosity reduction is between 30% and 70% relative to the viscosity of the initial solution.

4. The process as claimed in claim 1, wherein the protein comprising at least one antibody fragment is a protein selected from the group consisting of monoclonal antibodies (mAbs), polyclonal antibodies, fusion proteins, nanobodies, bispecific antibodies and antibodies coupled to cytotoxic active principles (ADC).

5. The process as claimed in claim 1, wherein the protein comprising at least one antibody fragment is a monoclonal antibody.

6. The process as claimed in claim 1, wherein the compound is chosen from the compounds of formula I in which the groups $R_1$, $R_2$ and $R_3$, which may be identical or different, are not a hydrogen atom.

7. The process as claimed in claim 1, wherein the compound is chosen from the compounds of formula I in which at least one group $R_4$, $R_5$, $R_6$ or $R_7$ is not a hydrogen atom, and comprises an amine N-oxide function.

8. The process as claimed in claim 1, wherein the compound is chosen from the compounds of formula II:

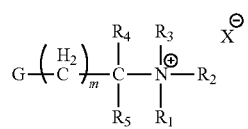

Formula II in which:

G is a C6 to C10 phenyl or alkylphenyl group, the phenyl group optionally being substituted with one or more hydroxyl groups, m is an integer equal to 0 or 1, $R_1$, $R_2$ and $R_3$, which may be identical or different, are either a hydrogen atom or a chain comprising 1 to 4 carbon atoms, said chain optionally comprising one or more heteroatoms N or O, $R_4$ is a chain comprising from 1 to 6 carbon atoms, said chain optionally comprising one or more heteroatoms N or O, but does not bear any carboxylic acid functions, $R_5$ is either a hydrogen atom or a chain comprising 1 to 6 carbon atoms, said chain optionally comprising one or more heteroatoms N or O, but does not bear any carboxylic acid functions, $X^-$ is an anion chosen from the group consisting of halides, carboxylates, sulfates, phosphates and sulfonates, the asymmetric carbon atoms have an R or S configuration.

9. The process as claimed in claim 1, wherein the compound is chosen from the compounds of formula IX:

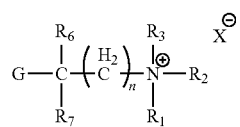

Formula IX in which:

G is a C6 to C10 phenyl or alkylphenyl group, the phenyl group optionally being substituted with one or more hydroxyl groups, n is an integer equal to 1, $R_1$, $R_2$ and $R_3$, which may be identical or different, are either a hydrogen atom or a chain comprising 1 to 4 carbon atoms, said chain optionally comprising one or more heteroatoms N or O, $R_6$ is a chain comprising 1 to 6 carbon atoms, said chain optionally comprising one or more heteroatoms N or O, but does not bear any carboxylic acid functions, $R_7$ is either a hydrogen atom or a chain comprising 1 to 6 carbon atoms, said chain optionally comprising one or more heteroatoms N or O, but does not bear any carboxylic acid functions, $X^-$ is an anion chosen from the group consisting of halides, carboxylates, sulfates, phosphates and sulfonates, the asymmetric carbon atoms have an R or S configuration.

10. The process as claimed in claim 1, wherein the compound is chosen from the compounds of formula III:

$$G-\left(\overset{H_2}{\underset{}{C}}\right)_m-\left(\overset{H}{\underset{R_5}{C}}\right)_n-\overset{R_3}{\underset{R_1}{\overset{|}{N^\oplus}}}-R_2 \quad X^\ominus \qquad \text{Formula III}$$

in which:
G is a C6 to C10 phenyl or alkylphenyl group, the phenyl group optionally being substituted with one or more hydroxyl groups,
m and n are integers, which may be identical or different, between 0 and 2 such that 0<m+n≤3,
$R_1$, $R_2$ and $R_3$, which may be identical or different, are either a hydrogen atom or a chain comprising 1 to 4 carbon atoms, said chain optionally comprising one or more heteroatoms N or O,
$R_5$ is either a hydrogen atom or an alkyl chain of 1 to 2 carbon atoms,
$X^-$ is an anion chosen from the group consisting of halides, carboxylates, sulfates, phosphates and sulfonates,
the asymmetric carbon atoms have an R or S configuration.

11. The process as claimed in claim 1, wherein the compound is chosen from the compounds of formula IV:

$$G-\left(\overset{H_2}{\underset{}{C}}\right)_m-\overset{R_4}{\underset{R_5}{\overset{|}{C}}}-\overset{R_3}{\underset{R_1}{\overset{|}{N^\oplus}}}-R_2 \quad X^\ominus \qquad \text{Formula IV}$$

in which:
G is a C6 to C10 phenyl or alkylphenyl group, the phenyl group being substituted with one or more hydroxyl groups,
m is an integer equal to 0 or 1,
$R_1$, $R_2$ and $R_3$, which may be identical or different, are either a hydrogen atom or a chain comprising 1 to 4 carbon atoms, said chain optionally comprising one or more heteroatoms N or O,
$R_4$ is a chain comprising 1 to 6 carbon atoms, said chain optionally comprising one or more heteroatoms N or O, but does not bear any carboxylic acid functions,
$R_5$ is either a hydrogen atom or a chain comprising 1 to 6 carbon atoms, said chain optionally comprising one or more heteroatoms N or O, but does not bear any carboxylic acid functions,
$X^-$ is an anion chosen from the group consisting of halides, carboxylates, sulfates, phosphates and sulfonates,
the asymmetric carbon atoms have an R or S configuration.

12. The process as claimed in claim 1, wherein the compound is chosen from the compounds of formula V:

$$G-\left(\overset{H_2}{\underset{}{C}}\right)_m-\overset{R_4}{\underset{R_5}{\overset{|}{C}}}-\overset{R_3}{\underset{R_1}{\overset{|}{N^\oplus}}}-R_2 \quad X^\ominus \qquad \text{Formula V}$$

in which:
G is a C6 to C10 phenyl or alkylphenyl group,
m is an integer equal to 0 or 1,
$R_1$, $R_2$ and $R_3$, which may be identical or different, are either a hydrogen atom or a chain comprising 1 to 4 carbon atoms, said chain optionally comprising one or more heteroatoms N or O,
$R_4$ is a chain comprising 1 to 6 carbon atoms, said chain optionally comprising one or more heteroatoms N or O, but does not bear any carboxylic acid functions,
$R_5$ is either a hydrogen atom or a chain comprising 1 to 6 carbon atoms, said chain optionally comprising one or more heteroatoms N or O, but does not bear any carboxylic acid functions,
$X^-$ is an anion chosen from the group consisting of halides, acetates, sulfates, phosphates and sulfonates,
the asymmetric carbon atoms have an R or S configuration.

13. The process as claimed in claim 1, wherein the compound is chosen from the compounds of formula XII:

$$G-\overset{H_2}{\underset{}{C}}-\overset{R_4}{\underset{H}{\overset{|}{C}}}-\overset{R_3}{\underset{R_1}{\overset{|}{N^\oplus}}}-R_2 \quad X^\ominus \qquad \text{Formula XII}$$

in which:
G is a C6 to C10 phenyl or alkylphenyl group, the phenyl group optionally being substituted with one or more hydroxyl groups,
$R_1$, $R_2$ and $R_3$, which may be identical or different, are either a hydrogen atom or a chain comprising 1 to 4 carbon atoms, said chain optionally comprising one or more heteroatoms N or O,
$R_4$ is a chain comprising 1 to 6 carbon atoms, said chain optionally comprising one or more heteroatoms N or O, but does not bear any carboxylic acid functions,
$X^-$ is at least one anion chosen from the group consisting of halides, carboxylates, sulfates, phosphates and sulfonates,
the asymmetric carbon atoms have an R or S configuration.

14. The process as claimed in claim 1, wherein the compound is chosen from the compounds of formula XIII:

$$G-\overset{H_2}{\underset{}{C}}-\overset{R_4}{\underset{H}{\overset{|}{C}}}-\overset{R_3}{\underset{R_1}{\overset{|}{N^\oplus}}}-R_2 \quad X^\ominus \qquad \text{Formula XIII}$$

in which:
G is a C6 to C10 phenyl or alkylphenyl group, the phenyl group optionally being substituted with one or more hydroxyl groups,
$R_1$, $R_2$ and $R_3$, which may be identical or different, are either a hydrogen atom or a chain comprising 1 to 4 carbon atoms, said chain optionally comprising one or more heteroatoms N or O,
$R_4$ is a chain comprising 1 to 6 carbon atoms, said chain comprising one or more heteroatoms N or O, an amine N-oxide function, but does not bear any carboxylic acid functions, X⁻ is at least one anion chosen from the group consisting of halides, carboxylates, sulfates, phosphates and sulfonates, the asymmetric carbon atoms have an R or S configuration.

15. The process as claimed in claim 1, wherein the compound is chosen from the compounds of formula XIV:

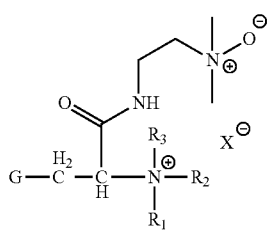

Formula XIV in which:
G is a C6 to C10 phenyl or alkylphenyl group, the phenyl group optionally being substituted with one or more hydroxyl groups,
$R_1$, $R_2$ and $R_3$, which may be identical or different, are either a hydrogen atom or a chain comprising 1 to 4 carbon atoms, said chain optionally comprising one or more heteroatoms N or O,
X⁻ is at least one anion chosen from the group consisting of halides, carboxylates, sulfates, phosphates and sulfonates,
the asymmetric carbon atoms have an R or S configuration.

16. The process as claimed in claim 1, wherein the compound is chosen from the compounds of formula XV:

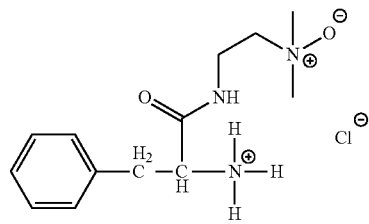

Formula XV in which:
the asymmetric carbon atoms have an R or S configuration.

17. The process as claimed in claim 1, wherein the compound is chosen from the compounds of formula X:

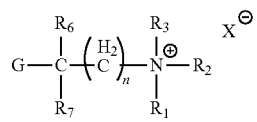

Formula X in which:
G is a C6 to C10 phenyl or alkylphenyl group, the phenyl group being substituted with one or more hydroxyl groups,
n is an integer equal to 1,
$R_1$, $R_2$, $R_3$, which may be identical or different, are either a hydrogen atom or a chain comprising 1 to 4 carbon atoms, said chain optionally comprising one or more heteroatoms N or O, $R_6$ is a chain comprising 1 to 6 carbon atoms, said chain optionally comprising one or more heteroatoms N or O, but does not bear any carboxylic acid functions,
$R_7$ is either a hydrogen atom or a chain comprising 1 to 6 carbon atoms, said chain optionally comprising one or more heteroatoms N or O, but does not bear any carboxylic acid functions,
X⁻ is an anion chosen from the group consisting of halides, carboxylates, sulfates, phosphates and sulfonates,
the asymmetric carbon atoms have an R or S configuration.

18. The process as claimed in claim 1, wherein the compound is chosen from the compounds of formula XI:

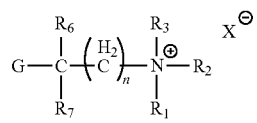

Formula XI in which:
G is a C6 to C10 phenyl or alkylphenyl group,
n is an integer equal to 1,
$R_1$, $R_2$ and $R_3$, which may be identical or different, are either a hydrogen atom or a chain comprising 1 to 4 carbon atoms, said chain optionally comprising one or more heteroatoms N or O,
$R_6$ is a chain comprising 1 to 6 carbon atoms, said chain optionally comprising one or more heteroatoms N or O, but does not bear any carboxylic acid functions,
$R_7$ is either a hydrogen atom or a chain comprising 1 to 6 carbon atoms, said chain optionally comprising one or more heteroatoms N or O, but does not bear any carboxylic acid functions,
X⁻ is an anion chosen from the group consisting of halides, carboxylates, sulfates, phosphates and sulfonates,
the asymmetric carbon atoms are of R or S configuration.

19. The process as claimed in claim 1, wherein the compound is chosen from the compounds of formula VII:

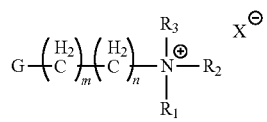

Formula VII in which:
G is a C6 to C10 phenyl or alkylphenyl group, the phenyl group optionally being substituted with one or more hydroxyl groups,
m and n are integers, which may be identical or different, between 0 and 2 such that 0<m+n≤3,
$R_1$, $R_2$, $R_3$, which may be identical or different, are either a hydrogen atom or a chain comprising 1 to 4 carbon atoms, said chain optionally comprising one or more heteroatoms N or O,
X⁻ is an anion chosen from the group consisting of halides, carboxylates, sulfates, phosphates and sulfonates,
the asymmetric carbon atoms have an R or S configuration.

20. The process as claimed in claim 1, wherein the compound is chosen from the compounds of formula VIII:

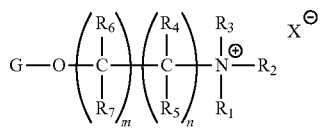

Formula VIII in which:

G is a C6 to C10 phenyl or alkylphenyl group, the phenyl group optionally being substituted with one or more hydroxyl groups, m and n are integers, which may be identical or different, between 0 and 2 such that 0<m+n≤3, $R_1$, $R_2$, $R_3$, which may be identical or different, are either a hydrogen atom or a chain comprising 1 to 4 carbon atoms, said chain optionally comprising one or more heteroatoms N or O, $R_4$, $R_5$, $R_6$ and $R_7$, which may be identical or different, are either a hydrogen atom or a chain comprising 1 to 6 carbon atoms, said chain optionally comprising one or more heteroatoms N or O, but does not bear any carboxylic acid functions, X⁻ is an anion chosen from the group consisting of halides, carboxylates, sulfates, phosphates and sulfonates, the asymmetric carbon atoms have an R or S configuration.

21. A process for lowering the viscosity, comprising preparing a solution comprising a compound of formula I

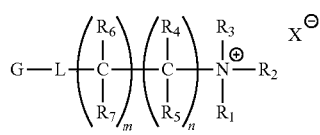

Formula I in which:

G is a C6 to C10 phenyl or alkylphenyl group, the phenyl group optionally being substituted with one or more hydroxyl groups, L is either a bond or a function chosen from the group consisting of the ether function, the carbamate function and the amide function, m and n are identical or different integers between 0 and 2 such that 0<m+n≤3, $R_1$, $R_2$ and $R_3$, which may be identical or different, are either a hydrogen atom or a chain comprising 1 to 4 carbon atoms, said chain optionally comprising one or more N or O heteroatoms, $R_4$, $R_5$, $R_6$ and $R_7$, which may be identical or different, are either a hydrogen atom or a chain comprising 1 to 6 carbon atoms, but does not bear any carboxylic acid functions, X⁻ is an anion chosen from the group consisting of halides, carboxylates, sulfates, phosphates and sulfonates, the asymmetric carbon atoms have an R or S configuration, and a protein comprising at least one antibody fragment whose concentration is between 50 and 350 mg/mL and whose pH is between 5 and 8.

22. The process as claimed in claim 21, wherein the compound of formula I and the protein comprising at least one antibody fragment whose concentration is between 50 and 350 mg/mL and whose pH is between 5 and 8 are added to a solution which is difficult to inject, this addition lowering the viscosity of the solution by a value of at least 15% relative to the viscosity of a solution of at least one protein comprising at least one antibody fragment of the same concentration and of the same pH not containing said compound.

23. The process as claimed in claim 21, wherein the concentration of the compound of formula I in the final formulation is between 10 and 250 mM.

24. The process as claimed in claim 21, wherein the concentration of the compound of formula I in the final formulation is between 100 and 200 mM.

25. A viscosity-reducing compound of formula XIV:

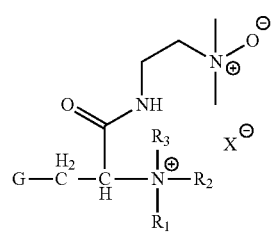

Formula XIV in which:

G is a C6 to C10 phenyl or alkylphenyl group, the phenyl group optionally being substituted with one or more hydroxyl groups, $R_1$, $R_2$ and $R_3$, which may be identical or different, are either a hydrogen atom or a chain comprising 1 to 4 carbon atoms, said chain optionally comprising one or more heteroatoms N or O, X⁻ is at least one anion chosen from the group consisting of halides, carboxylates, sulfates, phosphates and sulfonates, and the asymmetric carbon atoms have an R or S configuration.

26. A viscosity-reducing compound of formula XV:

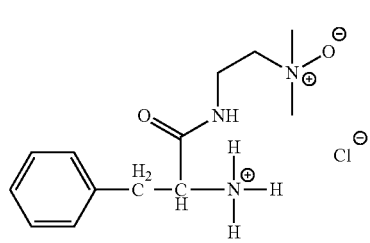

Formula XV in which:

the asymmetric carbon atoms have an R or S configuration.

27. An aqueous (reduced-viscosity) composition, containing a compound of formula XIV

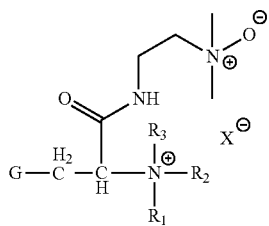

Formula XIV in which:
G is a C6 to C10 phenyl or alkylphenyl group, the phenyl group optionally being substituted with one or more hydroxyl groups,
$R_1$, $R_2$ and $R_3$, which may be identical or different, are either a hydrogen atom or a chain comprising 1 to 4 carbon atoms, said chain optionally comprising one or more heteroatoms N or O,
$X^-$ is at least one anion chosen from the group consisting of halides, carboxylates, sulfates, phosphates and sulfonates, and
the asymmetric carbon atoms have an R or S configuration,
and a protein comprising at least one antibody fragment whose concentration is between 50 and 350 mg/mL and whose pH is between 5 and 8.

28. The composition as claimed in claim 27, wherein the concentration of the compound of formula XIV is between 10 and 200 mM.

29. An aqueous (reduced-viscosity) composition, containing a compound of formula XV

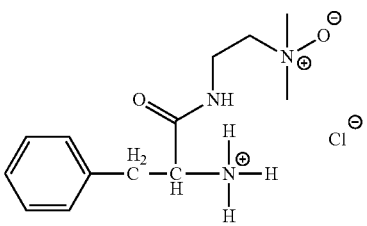

Formula XV in which:
the asymmetric carbon atoms have an R or S configuration,
and a protein comprising at least one antibody fragment whose concentration is between 50 and 350 mg/mL and whose pH is between 5 and 8.

30. The composition as claimed in claim 29, wherein the concentration of the compound of formula XV is between 10 and 200 mM.

* * * * *